United States Patent
Watts et al.

(10) Patent No.: US 10,457,653 B2
(45) Date of Patent: Oct. 29, 2019

(54) ADENYLYL CYCLASE INHIBITORS FOR CHRONIC PAIN AND OPIOID DEPENDENCE

(71) Applicant: Purdue Research Foundation, West Lafayette, IN (US)

(72) Inventors: Val J. Watts, West Lafayette, IN (US); Richard M. van Rijn, West Lafayette, IN (US); Daniel Patrick Flaherty, West Lafayette, IN (US); Jatinder Kaur, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/023,477

(22) Filed: Jun. 29, 2018

(65) Prior Publication Data
US 2019/0002418 A1    Jan. 3, 2019

Related U.S. Application Data

(60) Provisional application No. 62/527,059, filed on Jun. 30, 2017.

(51) Int. Cl.
| | | |
|---|---|---|
| *C07D 271/113* | (2006.01) | |
| *C07D 413/04* | (2006.01) | |
| *A61K 45/06* | (2006.01) | |
| *A61P 29/00* | (2006.01) | |
| *A61K 31/4245* | (2006.01) | |

(52) U.S. Cl.
CPC ...... *C07D 271/113* (2013.01); *A61K 31/4245* (2013.01); *A61K 45/06* (2013.01); *A61P 29/00* (2018.01); *C07D 413/04* (2013.01)

(58) Field of Classification Search
CPC .................. C07D 271/113; C07D 413/04
See application file for complete search history.

(56) References Cited

PUBLICATIONS

Cheng et al. (Bioorganic & Medicinal Chemistry, 2010, 18, 8512-8529).*
R.C. Reynolds et al. (Tuberculosis, 2012, 92, 72-83).*
Zhuo, M., (2012), Targeting neuronal adenylyl cylcase for the treatment of chronic pain, Drug Discov Today 17:573-582.
Sadana, R., (2009), Physiological Roles for G Protein-Regulated Adenylyl Clyclase Isoforms: Insights from Knockout and Overexpression Studies, Neurosignals 17:5-22.
Willougby, D., (2007), Organization and Ca2+ Regulation of Adenylyl Clyclases in cAMP Microdomains, Physiol Rev 87:965-1010).
Sababra, C., (2011), Neuroanatomical distribution and neurochemical characterization of cells expressing adenylyl cyclase isoforms in mouse and rat brain, J Chem Neuroanat 41:43-54.
Defer, N., (2000) Tissue specificity and physiological relevance of various isoforms of adenylyl cyclase, Am J Physiol Renal Physiol, 279:F400-F416.
Bosse, K., (2017), Adenylyl Cyclase 1 Is Required for Ethanol-Induced Locomotor Sensitization and Associated Increases in NMDA Receptor Phosphorylation and Function in the Dorsal Medial Striatum, J. Pharmacol. Exp. Ther. 2017, 363 (2) 148-155.
Sethna, F., (2017), Enhanced expression of ADCY1 underlies aberrant neuronal signalling and behaviour in a syndromic autism model, Nat. Commun., 8, 14359.
Kang, W., (2016), Analgesic effects of adenylyl cyclase inhibitor NB001 on bone cancer pain in a mouse model, Mol Pain 12., 1-9.
Corder, G., (2013), Constitutive μ-Opioid Receptor Activity Leads to Long-Term Endogenous Analgesia and Dependence, Science 341:1394-1399.
Baell, J., (2010), New Substructure Filters for Removal of Pan Assay Interference Compounds (PAINS) from Screening Libraries and for Their Exclusion in Bioassays., J. Med. Chem., 53, 2719-2740.
Cumbay, M., (2001), Heterologous Sensitization of Recombinant Adenylate Cyclases by Activation of D2 Dopamine Receptors, J. Pharmacol Exp Ther 297:1201-1399.
Masada, N., 2012, Distinct Mechanisms of Calmodulin Binding and Regulation of Adenylyl Clyclases 1 and 8, Biochemistry 51:7917-7929.
Tain, Z., (2015), Analgesic effects of NB001 on mouse models of arthralgia, Mol Brain 8:60, pp. 10.
Whittington, C.F., et al., Oligomers Modulate Intertibril Branching and Mass Transport Properties of Collagen Matrices, Microsc. Microanal. 19, 1323-1333 (2013).

* cited by examiner

*Primary Examiner* — Brian E McDowell
(74) *Attorney, Agent, or Firm* — Purdue Research Foundation; Liang Zeng Yan

(57) ABSTRACT

This present application disclosed a series of selective adenylyl cyclase 1 (AC1) inhibitors, compounds having a formula

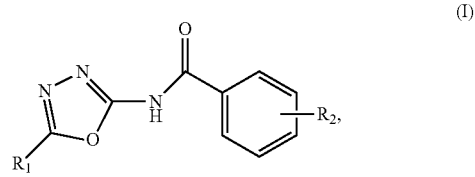

(I)

or a pharmaceutically acceptable salt thereof, as a pain therapeutic. Those compounds may provide an effective method of treatment for chronic/inflammatory pain. Those compounds may also prevent opioid dependence and/or reduce opioid dependence. Both method and composition matters are within the scope of this invention.

2 Claims, 2 Drawing Sheets

F0608-0538

F2209-0107

F0608-0011

F0559-0146

ADENYLYL CYCLASE INHIBITORS FOR CHRONIC PAIN AND OPIOID DEPENDENCE

CROSS REFERENCE TO RELATED APPLICATIONS

This present patent application relates to and claims the priority benefit of U.S. Provisional Application Ser. No. 62/515,571, filed Jun. 6, 2017, the contents of which are hereby incorporated herein by reference in their entirety.

GOVERNMENT SUPPORT CLAUSE

This invention was made with government support under MH101673 awarded by the National Institute of Health. The government has certain rights in the invention.

GOVERNMENT SUPPORT CLAUSE

This invention was made with government support under MH101673 awarded by the National Institute of Health. The government has certain rights in the invention.

TECHNICAL FIELD

The present disclosure generally relates to compounds as an adenylyl cyclase inhibitor useful for the treatment of chronic pain and opioid dependence. The invention described herein also pertains to pharmaceutical compositions and methods for treating diseases in mammals using compounds disclosed herein.

BACKGROUND AND SUMMARY

This section introduces aspects that may help facilitate a better understanding of the disclosure. Accordingly, these statements are to be read in this light and are not to be understood as admissions about what is or is not prior art.

Chronic pain is a major health concern that costs the US more than $635 billion per year (Gaskin and Richard, (2012) *J. Pain* 13:715-724). In addition to the financial impact, patients with chronic pain suffer extreme physical, emotional, and social burdens. For example, individuals often become socially isolated and confined to home as a result of their chronic pain that is not well-controlled by today's available treatments. The drugs used for the management of chronic pain include opioid analgesics, neuronal stabilizers such as anticonvulsants, and antidepressants. Opioids are the most widely used, and a recent NIH report indicates that there are significant problems associated with long-term opioid therapy for chronic pain (Volkow and McLellan (2016) *N Engl J Med* 374:1253-1263.). None of the agents provide sufficient relief to allow patients to return to their normal activity level. Moreover, current pharmaceutical industry has retreated from studying novel pain therapeutics due to the enormous risk (Skolnick and Volkow (2016) *Neuron* 92:294-297.). These observations indicate an essential need to identify new agents acting on unique targets in the war on chronic pain.

Adenylyl cyclases are enzymes that catalyze the production of cyclic adenosine monophosphate, an important biological messenger. There are nine different membrane-bound human adenylyl cyclase isoforms, each with slightly different attributes. In particular, adenylyl cyclase 1 (AC1) is highly expressed in the hippocampus as well as in regions of the brain associated with pain. AC1 knock out animals show reduced neuropathic and inflammatory pain. Additionally, AC1 knock out mice show less reward when given opioids and show reduced symptoms of opioid dependence during withdrawal. Additional reports suggest that AC1 inhibition may also provide a useful therapeutic intervention for alcohol use disorder and autism (Bosse K E et al., *J. Pharmacol. Exp. Ther.* 2017, 363 (2) 148-155; Sethna F., et al. *Nat. Commun.* 2017, 8, 14359).

Unfortunately, until now, the selective inhibition of ACs has not been achieved, and simultaneous inhibition of multiple adenylyl cyclase isoforms would likely result in significant adverse effects. There are unmet needs for better and safer medications targeting adenylyl cyclases for various therapeutic uses.

DETAILED DESCRIPTION

Figure 1:
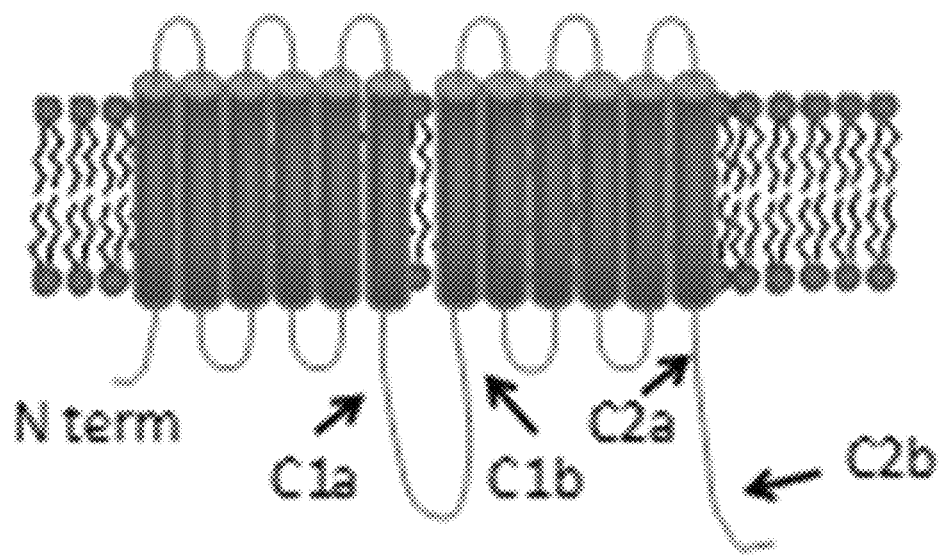
FIG. 1 depicts structure of membrane-bound adenylyl cyclases.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH═CH—, —CH═CHCH$_2$—, and the like. Examples of branched alkenyl groups include, but are not limited to, —CH═C(CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R-NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $-NH_2$, $-NHR$, $-NR_2$, $-NR_3^+$, wherein each R is independently selected, and protonated forms of each, except for $-NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, $-CF(CH_3)_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, the invention is related to a compound of formula (I)

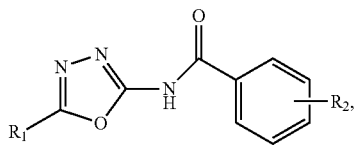

(I)

or a pharmaceutically acceptable salt thereof, wherein $R_1$ is an alkyl, alkenyl, alkynyl, heteroalkyl, heteroalkenyl, heteroalkynyl, cycloalkyl, heterocyloalkyl, cycloalkenyl, heterocycloakenyl, heterocyclyl, or an optionally substituted aryl, arylalkyl, or arylalkenyl; and $R_2$ represents five substituents independently selected from the group consisting of hydrogen, halo, hydroxy, amino, nitro, cyano, thio, alkyl, alkenyl, alkynyl, heteroalkyl, heteroalkenyl, heteroalkynyl, cycloalkyl, heterocyloalkyl, cycloalkenyl, heterocycloakenyl, heterocyclyl, alkoxyl, alkylamino, alkylthio, haloalkyl, alkylsulfide, sulphonyl, sulphonamide, alkylsulphonamide, or an optionally substituted aryl, arylalkyl, or arylalkenyl; or any two adjacent substituents that are taken together with the attached carbons to form an optionally substituted cycle or heterocycle and each of other substituents is defined as above.

In some other embodiments, this invention is related to compounds having a general formula (I), wherein $R_1$ is a $C_1$-$C_{24}$ alkyl, cycloalkyl, or an optionally substituted $C_4$-$C_{24}$ aryl or heteroaryl.

In some other embodiments, this invention is related to compounds having a general formula (I), wherein $R_1$ is an optionally substituted $C_4$-$C_{24}$ aryl or heteroaryl.

In some other embodiments, this invention is related to compounds having a general formula (I), wherein $R_1$ is a $C_4$-$C_{24}$ alkyl or cycloalkyl, which is optionally substituted.

In some other embodiments, this invention is related to compounds having a general formula (I), wherein one or more of the five $R_2$ substituents are an alkylsulfide, sulfonamide or alkylsulfonamide, and the other substituents are hydrogen.

In some other embodiments, this invention is related to compounds having a general formula (I), wherein one or more of the five $R_2$ substituents are a halo or haloalkyl, and the other substituents are hydrogen.

In some other embodiments, this invention is related to compounds having a general formula (I), wherein the compounds are selected from the group consisting of

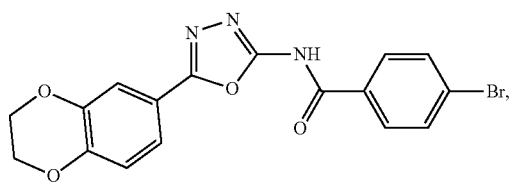

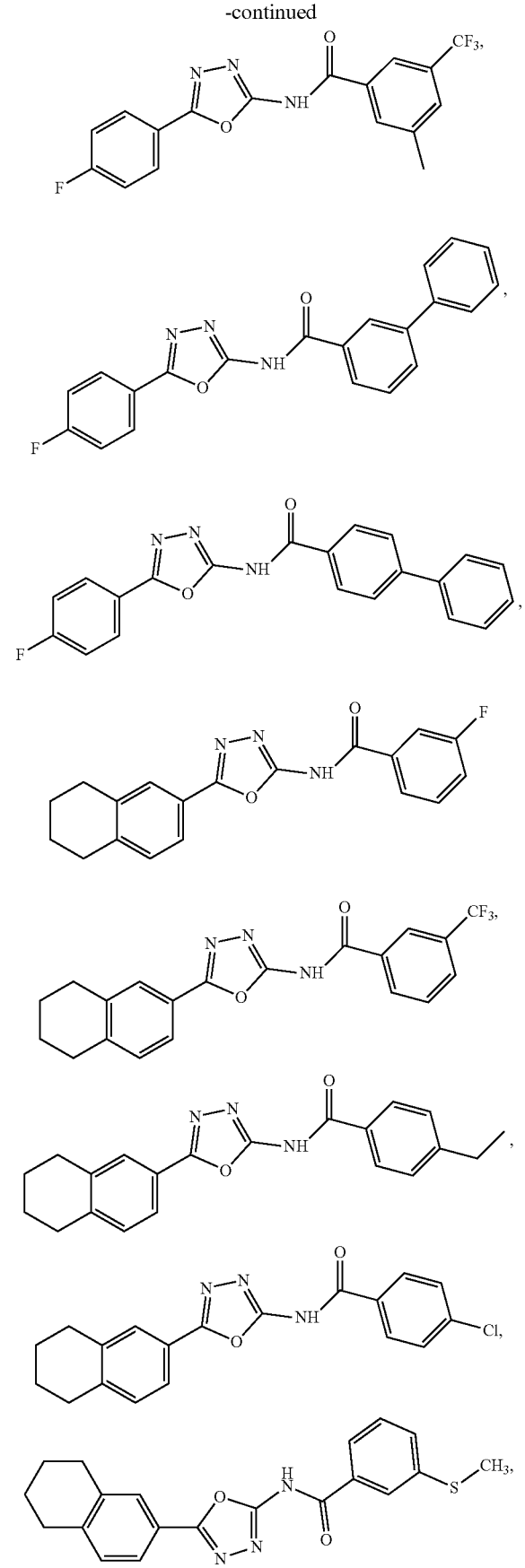

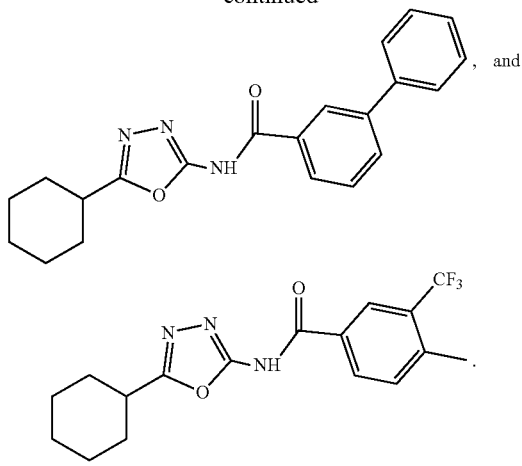

In some other embodiments, this invention is related to a pharmaceutical composition comprising one or more compounds disclosed herein, or a pharmaceutically acceptable salt thereof, together with one or more diluents, excipients or carriers.

In some other embodiments, this invention is related to a pharmaceutical composition comprising one or more compounds disclosed herein, or a pharmaceutically acceptable salt thereof, in combination with one or more other compounds by the same or different mode of action, together with one or more diluents, excipients or carriers.

In some embodiments, this invention is related to a method for treating pain, opioid dependence, alcohol use disorder, or autism comprising the step of administering to a patient in need thereof a therapeutically effective amount of one or more compounds of a mammal in need thereof a therapeutically effective amount of one or more compounds of formula (I)

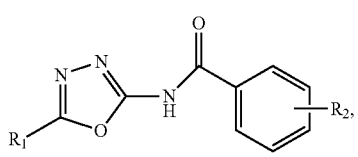

or a pharmaceutically acceptable salt thereof, and one or more carriers, diluents, or excipients, wherein
$R_1$ is an alkyl, alkenyl, alkynyl, heteroalkyl, heteroalkenyl, heteroalkynyl, cycloalkyl, heterocyloalkyl, cycloalkenyl, heterocycloakenyl, heterocyclyl, or an optionally substituted aryl, arylalkyl, or arylalkenyl; and
$R_2$ represents five substituents independently selected from the group consisting of hydrogen, halo, hydroxy, amino, nitro, cyano, thio, alkyl, alkenyl, alkynyl, heteroalkyl, heteroalkenyl, heteroalkynyl, cycloalkyl, heterocyloalkyl, cycloalkenyl, heterocycloakenyl, heterocyclyl, alkoxyl, alkylamino, alkylthio, haloalkyl, alkylsulfide sulphonyl, sulfonamide, alkylsulfonamide, or an optionally substituted aryl, arylalkyl, or arylalkenyl; or any two adjacent substituents that are taken together with the attached carbons to form an optionally substituted cycle or heterocycle and each of other substituents is defined as above.

In some other embodiments, this invention is related to a method for treating a chronic pain using an AC1 inhibitor.

In some other embodiments, this invention is related to a method for treating and reducing pain and opioid dependence using an AC1 inhibitor.

In some other embodiments, this invention is related to a method for treating autism using an AC1 inhibitor.

In some other embodiments, this invention is related to a method for treating alcohol use disorder using an AC1 inhibitor.

In some embodiments, this invention is related to a method for treating and reducing pain and opioid dependence further comprising the step of administering a compound of formula I in combination with an opioid drug, wherein said compound of formula I enhances µ-opioid receptor inhibition of adenylyl cyclase 1.

In some other embodiments, this invention is related to a method for treating and reducing pain and opioid dependence, wherein the opioid drug is selected from the group consisting of codeine, morphine, thebaine, oripavine, diacetylmorphine, nicomorphine, dipropanoylmorphine, diacetyldihydromorphine, acetylpropionylmorphine, desomorphine, methyldesorphine, dibenzoylmorphine, dihydrocodeine, ethylmorphine, heterocodeine, buprenorphine, etorphine, hydrocodone, hydromorphone, oxycodone, oxymorphone, fentanyl, alphamethylfentanyl, alfentanil, sufentanil, remifentanil, carfentanil, ohmefentanyl, pethidine (meperidine), ketobemidone, desmethylprodine (MPPP), allylprodine, prodine, phenethylphenylacetoxypiperidine (PEPAP), promedol, propoxyphene, dextropropoxyphene, dextromoramide, bezitramide, piritramide, methadone, dipipanone, levomethadyl acetate (LAAM), difenoxin, diphenoxylate, loperamide, dezocine, pentazocine, phenazocine, buprenorphine, dihydroetorphine, etorphine, butorphanol, nalbuphine, levorphanol, levomethorphan, lefetamine, menthol, meptazinol, mitragynine, tilidine, tramadol, tapentadol, eluxadoline, nalmefene, naloxone, and naltrexone.

In some other embodiments, this invention is related to a method for treating pain or opioid dependence comprising the step of administering to a patient in need thereof a therapeutically effective amount of one or more compounds disclosed herein, in combination with one or more other compounds by the same or different mode of action, and one or more carriers, diluents, or excipients, to a patient in need of relief from said disorder.

In addition, it is appreciated herein that the compounds described herein may be used in combination with other compounds that are administered to treat other symptoms, such as compounds administered to relieve nausea, vomiting, and the like.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Neurobiological, genetic, and preclinical studies have implicated neuronal adenylyl cyclase type I (AC1) as a potential new drug target (Zhuo (2012) *Drug Discov Today* 17:573-582.). Adenylyl cyclases (AC) are an enzyme family that serve as effectors of numerous G protein coupled receptors (e.g. opioid and dopamine receptors) and produce the second messenger cAMP from ATP (FIG. 1). Nine membrane-bound isoforms of AC share a similar structure that includes an intracellular N-terminus, followed by two membrane-spanning domains alternating with two cytoplasmic (catalytic) domains that can be further divided into a and b regions (Sadana and Dessauer, (2009) *Neurosignals* 17:5-

22.). The C1a and C2a domains make up the catalytic portion of the enzyme, and an X-ray crystal structure with the C1a domain from AC5 and the C2a domain from AC2 was solved in 1997 (Tesmer et al., (1997) *Science* 278:1907-1916.). In contrast, no structural information exists regarding N-terminus, C1b, or C2b domains for any isoform. Each isoform is uniquely regulated by G protein α and βγ subunits, $Ca^{2+}$, protein kinases, posttranslational modifications, and subcellular localization (Sadana R and Dessauer C W (2009). *Neurosignals* 17:5-22; Willoughby and Cooper, (2007) *Physiol Rev* 87:965-1010.). Group 1 ACs, which are represented by AC1, AC3, and AC8, are stimulated by calmodulin in a $Ca^{2+}$-dependent manner. Group 2 ACs are characterized by their conditional stimulation by Gβγ subunits and are represented by AC2, AC4, and AC7. AC2 and AC7 are also activated by protein kinase C. Group 3 ACs include AC5 and AC6, show robust negative regulation by $G\alpha_i$ subunits, and are also inhibited by submicromolar concentration of $Ca^{2+}$ as well as protein kinase A. Group 4 ACs contains only one member, AC9, which is unique among the ACs in being relatively insensitive to activation by the small molecule diterpene, forskolin.

Membrane-bound ACs are highly expressed in the central nervous system and generally have overlapping expression patterns (Sanabra and Mengod, (2011). *J Chem Neuroanat* 41:43-54.). Multiple AC isoforms are typically expressed in individual cell types, making it difficult to elucidate the function(s) of individual isoforms in either native tissues or cell lines. This problem has been addressed using a variety of recombinant approaches, including overexpression, site-directed mutagenesis, and, most notably, global genetic deletions. These animals lacking one or multiple AC isoforms have been essential tools to inform on the physiological roles of AC signaling in the central nervous system (Sadana R et al., (2009). *Neurosignals* 17:5-22).

Physiological Roles of AC and AC8:

AC1 and AC8 are robustly activated by $Ca^{2+}$/calmodulin ($Ca^{2+}$/CaM) and have overlapping expression patterns in neuronal tissues, including the hippocampus and several cortical regions (Defer N, et al., (2000). *Am J Physiol Renal Physiol* 279:F400-F416). To explore their relative physiological roles, a number of studies have been carried out with mice lacking either AC1 ($AC1^{-/-}$), AC8 ($AC8^{-/-}$), or both isoforms (double knock out mice, DKO). Initial experiments with animals lacking $Ca^{2+}$/CaM-stimulated cyclases were focused on long-term memory (LTM) and long-term potentiation (LTP) due to their high level of expression in the hippocampus. The results of these experiments implicated AC1 and AC8 in LTP and LTM (Ferguson and Storm, 2004). Importantly, it was found that long lasting LTP and memory deficits were marked in animals lacking both AC1 and AC8 (DKO mice), but were mostly absent in animals deficient in only a single AC isoform. However, a few studies found that $AC1^{-/-}$ mice showed modest deficits in other forms of LTP (Chen et al., (2014), *Mol Pain* 10:65.), including a reduction in remote contextual fear memory that was only observed at a single time point. These observations clearly implicate $Ca^{2+}$/CaM-stimulated cyclases in LTP and certain models of memory; however, selectively targeting a single AC isoform markedly reduces the overall deficits. Furthermore, these findings also emphasize the benefits of pharmacologically targeting overactive AC1 in dose-dependent fashion versus complete inhibition or genetic deletion.

The development and characterization of the $AC1^{-/-}$, $AC8^{-/-}$, and DKO mice also offered a powerful approach for identifying the molecular signaling roles for AC1 and AC8 in pain. AC1 and AC8 are not required for acute pain responses; however, behavioral responses to inflammatory stimuli (i.e. formalin and CFA) were nearly eliminated or abolished in $AC1^{-/-}$ or DKO mice, respectively (Wei et al., (2002) *Neuron* 36:713-726.). The lack of behavioral sensitization to pain in the knockout mice could not be explained by changes in physical tissue responses such as the degree of inflammation or plasma extravasation. Zhou and colleagues also used a muscle pain model to indicate that AC1 was essential for chronic inflammatory pain (Vadakkan et al., (2006). *Mol Pain* 2:7.). More recently, Dr. Taylor's team showed that $AC1^{-/-}$ mice were insensitive to CFA-induced allodynia (Corder et al., (2013) *Science* 341:1394-1399.). Although the precise role of AC1 in mediating chronic pain remains to be determined, several lines of evidence suggest that it may involve plasticity in the anterior cingulate cortex and spinal cord. Regardless of the mechanism, AC1 has been proposed to be a potential drug target for treating chronic pain based on the four criteria (Zhuo M (2012). *Drug Discov Today* 17:573-582.). First, AC1 is highly expressed in the CNS versus other tissues (e.g. heart, liver, or kidney) reducing side effects. Second, AC1 is regulated by $Ca^{2+}$/CaM in an activity-dependent fashion. Third, behavioral studies with the $AC1^{-/-}$ mice have implicated AC1 in chronic inflammatory and neuropathic pain. Fourth, studies in animals reveal that chronic pain stimuli increase cAMP signaling (Wei et al., (2002) *Neuron* 36:713-726). These observations support the idea that selective inhibitors of AC1 offer a new and safer pharmacological approach for treating chronic pain.

Adenylyl Cyclase Inhibitors as Potential Drugs.

Figure 2:
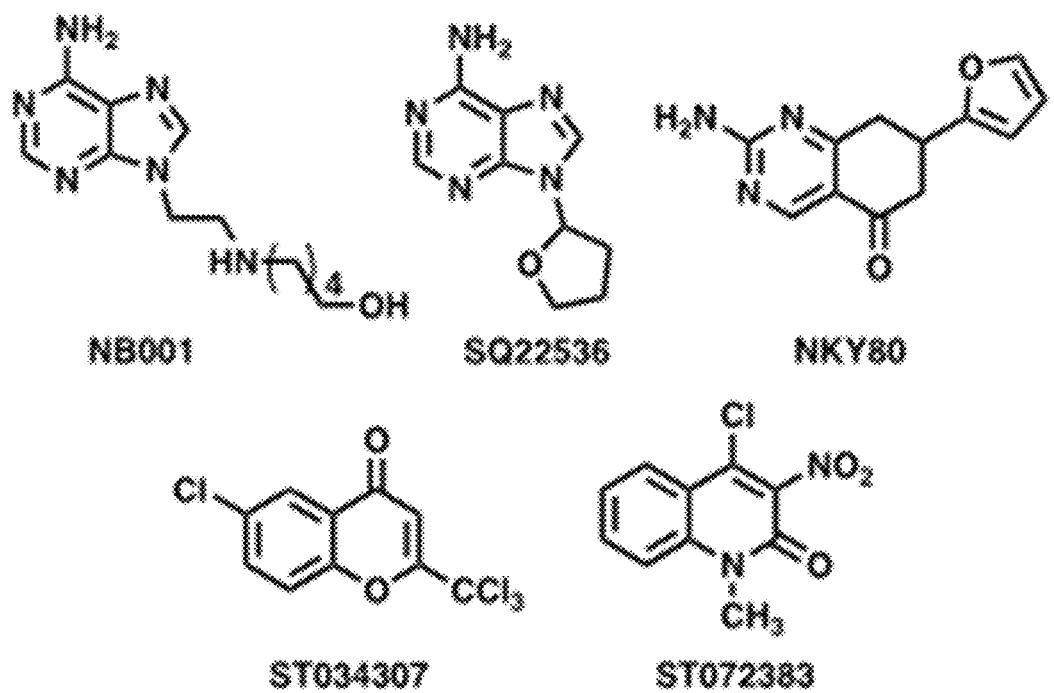
FIG. 2 shows structures of select adenine (NB001 and SQ22536) and non-adenine (NKY80, ST034307, and ST072383) AC inhibitors.

The observations described above led Dr. Zhuo and colleagues to identify and subsequently evaluate a small molecule inhibitor of AC1, NB001 (FIG. 2) in multiple chronic pain models (Kang et al., (2016) *Mol Pain* 12; Tian et al., (2015) *Mol Brain* 8:60). This molecule was identified from a search of forskolin- and adenosine triphosphate-like structures. NB001 was shown to have >10-fold selectivity for AC1 (IC50=10 μM) versus the closely related AC8 (IC50=139 uM) in HEK293 cells expressing recombinant AC isoforms. NB001 was shown to have activity consistent with AC1 inhibition in additional neuronal cell models (i.e. SH-SY5Y cells) and tissue preparations of the anterior cingulate cortex. Consistent with data from the $AC1^{-/-}$ mice, NB001 markedly attenuated chronic pain responses (i.e. inflammatory and neuropathic) in both mice and rats. More recent studies also suggest that NB001 has AC1 inhibitory activity in animal models of opiate dependence (Corder et al., (2013) *Science* 341:1394-1399.). These preclinical studies with NB001 implicate further AC1 as a potential new target for exploring inhibitors of chronic pain.

The development and mechanistic characterization of AC1-selective small molecule inhibitors is believed to provide novel non-opioid weapons in the war on chronic pain. We identified our initial hits via screening 10,000 selected compounds from the Life Chemicals collection. The screen was carried out using HEK cells stably expressing AC1 (HEK-AC1) and cyclic AMP accumulation was stimulated using the $Ca^{2+}$ ionophore, A23187 to selectively activate AC1. Compounds with potential chemical liabilities and PAINs were removed from further evaluation (Baell and Holloway, *J. Med. Chem.* 2010, 53, 2719-2740).

Fresh powders of several robust inhibitors (>90% inhibition) were evaluated in multiple confirmation assays assessing the dose response relationship for inhibiting AC1 and AC8 activity. Confirmation assays used A23817 to selectively stimulate recombinant AC1 or AC8 in the HEK cell background (Cumbay and Watts (2001), *J. Pharmacol Exp*

*Ther* 297:1201-1399). This approach takes advantage of one unique regulatory property of AC1 for the development of selective inhibitors. Both AC1 and AC8 are robustly activated by $Ca^{2+}$/CaM under a variety of conditions, whereas the effects of $Ca^{2+}$/CaM on AC3 are modest and conditional requiring activation by G proteins. Previous studies have identified unique $Ca^{2+}$/CaM binding domains as one possible site of interaction to achieve AC1 (vs. AC8) selectivity (Masada et al., 2012, *Biochemistry* 51:7917-7929). These observations suggest that AC1 selectivity can be achieved through targeting $Ca^{2+}$/CaM activation of AC1. In support of this, a portion of the hits identified for expansion herein revealed selective inhibition of $Ca^{2+}$/CaM-stimulated AC1 versus AC8 (Table 1).

Figure 3:
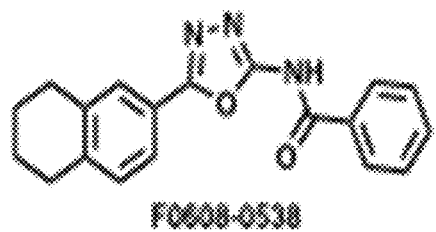
FIG. 3 depicts selected analogs representing Series 1 AC1 inhibitor scaffolds.
Figure 3:
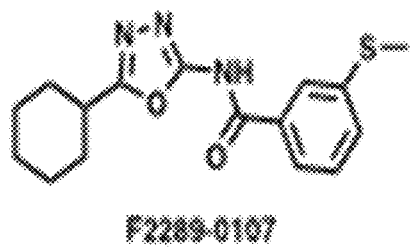
Figure 3:
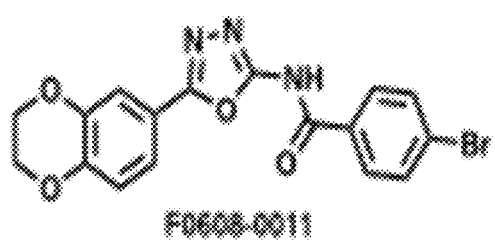
Figure 3:
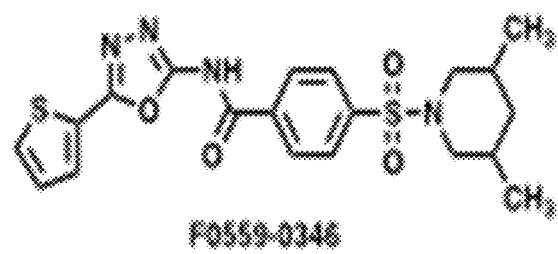

The primary technology we employed to measure cAMP accumulation was a homogenous time-resolved fluorescence (HTRF) assay, the same technology utilized in the primary screen. The activity of the new compounds was studied at AC1 and AC8 revealing a range of potency and activity patterns (Table 1 and FIG. 3). Subsequent assays for AC1 and AC8 using the HitHunter cAMP assay revealed similar rank-order potency and efficacy values (data not shown). The most potent and selective compounds F2215-0213 (Table 1 and FIG. 3) appears to be at least 60 fold selective for AC1 versus AC8. The second scaffold represented by F0608-0011 (FIG. 3) displayed slightly reduced potency and selectivity compared to the first. This could be due to either 1) the chemical scaffolds are exquisitely selective toward the AC family of enzymes or 2) the library has not been screened against a sufficient number of targets. The answer is likely a combination of the two; nonetheless, the lack of biological data to date bodes well for these series and any potential off-target promiscuity.

TABLE 1

Activity at AC1, AC8, AC2, and AC5 in stable HEK cell lines*

| Compd. | hAC1 IC$_{50}$ (µM) | hAC1 % Inhib. | hAC8[c] IC$_{50}$ (µM) | hAC8[c] % Inhib. | Selectivity AC1 vs AC8[d] | hAC2[c] % Inhib. | hAC5[c] % Inhib. | Viability[e] % Vehicle |
|---|---|---|---|---|---|---|---|---|
| ST034307[a] | 2.3 | 108 ± 10 | ND | −25 ± 1 | >13-fold | −142 | −44 | 85 ± 6 |
| F0608-0538[b] | 2.1 ± 0.4 | 101 ± 1 | 21 ± 4 | 76 ± 8 | 10-fold | −95 | −34 | 118 ± 6 |
| F0608-0011[b] | 2.0 ± 0.2 | 101 ± 1 | 18 ± 2 | 79 ± 1 | 9-fold | −7 | −10 | 125 ± 3 |
| F2289-0107[b] | 7.5 ± 2.0 | 99 ± 1 | ND | 31 ± 2 | >4-fold | −210 | −28 | 117 ± 1 |
| F0559-0346[b] | 9.1 ± 2.0 | 99 ± 1 | 17 ± 6 | 74 ± 13 | 2-fold | −6 | 4 | 118 ± 2 |
| F2215-0213[b] | 0.5 ± 0.1 | 99 ± 1 | ND | 20 ± 1 | >60-fold | −70 | 9 | 101 ± 17 |
| F2215-0772[b] | 0.9 ± 0.2 | 100 ± 1 | ND | 34 ± 7 | >30-fold | 32 | 13 | 93 ± 1 |
| F2215-0954[b] | 5.9 ± 0.4 | 99 ± 1 | ND | 35 ± 8 | >5-fold | −185 | −21 | 106 ± 14 |

*Cyclic AMP accumulation for AC1 or AC8 was stimulated using A23187. AC2 activity was stimulated with 100 nM PMA and AC5 activity was stimulated with 300 nM forskolin.
ND = not able to be determined.
[a]data from Brust et al., *Sci. Signal.* 21 Feb. 2017: Vol. 10, Issue 467, eaah5381);
[b]FIG. 3;
[c]% inhibition at 30 µM (negative values indicate a potentiated response);
[d]Selectivity = AC8 IC$_{50}$/AC1 IC$_{50}$, in the absence of IC$_{50}$ values at AC8, estimates based on IC$_{50}$ value of ≥ 30 µM;
[e]values determined in AC1-HEK cells.
All values based n ≥ 3, except AC2 and AC5 (n = 2).

TABLE 2

| compd ID | HEK-AC1 IC50 (µM) | HEK-AC1 % Inhibition (30 µM) | HEK-AC8 IC50 (µM) | HEK-AC8 % Inhibition (30 µM) | HEK-AC2 % Inhibition (10 µM) | HEK-AC2 % Inhibition (30 µM) |
|---|---|---|---|---|---|---|
| | | Activity Table of Compounds Disclosed | | | | |
| AC10001 | 31 ± 3 | 60 ± 3 | 102 ± 26 | 24 ± 7 | (−)276 ± 38 | (−)411 ± 63 |
| AC10002 | 3.4 ± 1 | 100 ± 1 | 19.1 ± 5 | 80 ± 6 | (−)214 ± 50 | (−)196 ± 8 |
| AC10003 | 24.5 ± 2 | 65 ± 4 | ND | 3 ± 6 | (−)43 ± 22 | (−)199 ± 43 |
| AC10004 | 29 ± 10 | 65 ± 8 | ND | 8 ± 2 | (−)22 ± 18 | (−)129 ± 28 |
| AC10005 | 12.2 ± 3 | 74 ± 4 | 27 ± 8 | 64 ± 13 | (−)217 ± 24 | (−)160 ± 23 |
| AC10006 | 29 ± 3 | 56 ± 5 | 101 ± 3 | 18 ± 2 | (−)134 ± 35 | (−)94 ± 45 |
| AC10007 | 8.6 ± 3 | 82 ± 7 | 25 ± 8 | 71 ± 11 | (−)188 ± 35 | (−)229 ± 37 |
| AC10008 | 10 ± 1 | 78 ± 3 | 71 ± 18 | 33 ± 3 | (−)150 ± 26 | (−)221 ± 14 |
| AC10009 | 7.7 ± 1 | 81 ± 1 | 55 ± 20 | 41 ± 9 | (−)167 ± 46 | (−)165 ± 5 |
| AC10010 | 9.9 ± 7 | 77 ± 13 | 12.6 ± 6 | 63 ± 7 | (−)148 ± 50 | (−)118 ± 1 |
| AC10011 | 6.6 ± 3 | 77 ± 8 | 61 ± 22 | 43 ± 6 | (−)202 ± 49 | (−)216 ± 46 |
| AC10012 | 11 ± 2 | 84 ± 5 | 66 ± 2 | 34 ± 1 | (−)138 ± 1 | 212 ± 49 |
| AC10013 | 1.7 ± 0.7 | 97 ± 4 | 9.4 ± 2 | 68 ± 5 | (−)278 ± 18 | (−)231 ± 75 |
| AC10014 | 3.4 ± 0.6 | 101 ± 0.4 | 23 ± 3 | 68 ± 0.5 | (−) 194 ± 35 | (−)198 ± 49 |
| AC10016 | 3.1 ± 0.4 | 99 ± 0 | 25 ± 4 | 55 ± 3 | (−)358 ± 143 | (−)283 ± 97 |
| AC10017 | 10.7 ± 2 | 84 ± 5 | 83 ± 22 | 35 ± 4 | (−)148 ± 81 | (−)214 ± 38 |
| AC10018 | 15 ± 2 | 80 ± 5 | ND | 10 ± 7 | (−)65 ± 22 | (−)209 ± 55 |
| AC10020 | 9.5 ± 1 | 88 ± 5 | 76 ± 39 | 37 ± 9 | (−)146 ± 26 | (−)360 ± 59 |
| AC10021 | 6 ± 0.6 | 99 ± 1 | 33 ± 8 | 62 ± 8 | (−)414 ± 78 | (−)570 ± 86 |
| AC10023 | 5.1 ± 0.7 | 100 ± 0.2 | 32 ± 12 | 60 ± 8 | (−)283 ± 56 | (−)339 ± 44 |
| AC10024 | 8.1 ± 2 | 85 ± 4 | 44 ± 6 | 57 ± 7 | (−)557 ± 92 | (−)684 ± 98 |
| AC10025 | 10.1 ± 1 | 86 ± 7 | 53 ± 21 | 35 ± 8 | (−)193 ± 56 | (−)496 ± 75 |

TABLE 2-continued

| | HEK-AC1 | | HEK-AC8 | | HEK-AC2 | |
| --- | --- | --- | --- | --- | --- | --- |
| compd ID | IC50 (μM) | % Inhibition (30 μM) | IC50 (μM) | % Inhibition (30 μM) | % Inhibition (10 μM) | % Inhibition (30 μM) |
| AC10026 | 1.6 ± 0.2 | 100 ± 1 | 7.9 ± 3 | 82 ± 7 | (−)571 ± 101 | (−)449 ± 73 |
| AC10028 | 5 ± 1 | 99 ± 2 | 29 ± 1 | 58 ± 1 | (−) 339 ± 47 | (−) 282 ± 76 |
| | | | Activity Table of Assays (Continued) | | | |
| AC10029 | 11.5 ± 4 | 86 ± 11 | 83 ± 47 | 25 ± 6 | (−) 102 ± 35 | (−)218 ± 32 |
| AC10030 | 6.5 ± 1 | 93 ± 4 | 46 ± 7 | 42 ± 4 | (−)301 ± 36 | (−)347 ± 32 |
| AC10031 | 7.3 ± 2 | 80 ± 10 | 61 ± 33 | 31 ± 6 | (−)237 ± 67 | (−)341 ± 58 |
| AC10032 | 15.8 ± 2 | 78 ± 4 | ND | 1 ± 12 | (−)276 ± 38 | (−)411 ± 63 |
| AC10033 | 3.4 ± 1 | 100 ± 1 | 25 ± 6 | 60 ± 8 | (−) 292 ± 39 | (−) 275 ± 51 |
| AC10034 | 15 ± 4 | 79 ± 9 | 101 ± 14 | 23 ± 5 | (−)134 ± 22 | (−) 204 ± 42 |
| AC10035 | 5.3 ± 0.4 | 100 ± 1 | 14 ± 3 | 61 ± 1 | (−) 401 ± 56 | (−) 301 ± 58 |
| AC10036 | 16 ± 4 | 83 ± 6 | 39 ± 16 | 38 ± 7 | (−) 156 ± 32 | (−)302 ± 52 |
| AC10037 | 7.5 ± 0.7 | 88 ± 3 | 56 ± 23 | 39 ± 7 | (−)154 ± 16 | (−)164 ± 21 |
| AC10038 | 9.6 ± 3 | 84 ± 5 | 115 ± 43 | 18 ± 10 | (−)178 ± 25 | (−)283 ± 64 |
| AC10039 | 13 ± 3 | 73 ± 4 | ND | 20 ± 6 | (−)76 ± 18 | (−)97 ± 25 |
| AC10040 | 22 ± 3 | 73 ± 1 | ND | 6 ± 16 | (−)65 ± 13 | (−)203 ± 39 |
| AC10041 | 6.4 ± 1 | 94 ± 2 | 46 ± 13 | 34 ± 11 | (−)246 ± 31 | (−)305 ± 30 |
| AC10044 | 8.2 ± 2 | 88 ± 4 | 51 ± 7 | 32 ± 12 | (−)180 ± 35 | (−)236 ± 42 |
| AC10045 | 7.3 ± 3 | 91 ± 4 | 71 ± 14 | 44 ± 7 | (−)279 ± 46 | (−) 388 ± 36 |
| AC10046 | 10.6 ± 3 | 81 ± 7 | 69 ± 11 | 35 ± 1 | (−)117 ± 19 | (−)186 ± 13 |
| AC10047 | 10.5 ± 2 | 79 ± 8 | ND | 11 ± 3 | (−)124 ± 33 | (−) 229 ± 30 |
| AC10052 | 17 ± 2 | 64 ± 1 | ND | 14 ± 3 | (−) 41 ± 28 | (−) 86 ± 26 |
| AC10053 | 12.8 ± 1 | 74 ± 3 | ND | 7 ± 4 | (−)117 ± 10 | (−)228 ± 19 |
| AC10054 | 8.9 ± 1 | 76 ± 1 | ND | 11 ± 9 | (−)163 ± 30 | (−)194 ± 5 |
| AC10055 | 13.5 ± 2 | 71 ± 5 | ND | 10 ± 12 | (−)122 ± 7 | (−) 157 ± 18 |
| AC10056 | 5.9 ± 1 | 98 ± 1 | 22 ± 4 | 74 ± 8 | (−)222 ± 24 | (−)244 ± 22 |
| AC10059 | 1.0 ± 0.3 | 99 ± 0.4 | 4.2 ± 0.2 | 90 ± 1 | (−)362 ± 26 | (−)276 ± 34 |
| AC10060 | ND | 12 ± 4 | ND | 13 ± 7 | 3 ± 6 | (−) 14 ± 8 |
| AC10061 | 1.5 ± 1 | 99 ± 1 | 3.6 ± 0.4 | 90 ± 0.4 | (−) 204 ± 39 | (−) 170 ± 26 |
| AC10062 | 1.2 ± 0.2 | 98 ± 1 | 2 ± 0.4 | 88 ± 2 | (−)187 ± 32 | (−)191 ± 59 |
| AC10063 | 1.4 ± 0.2 | 99 ± 1 | 1.4 ± 0.4 | 92 ± 1 | (−)388 ± 44 | (−) 339 ± 74 |
| AC10064 | 2.3 ± 0.4 | 98 ± 1 | 7 ± 1 | 84 ± 3 | (−) 164 ± 25 | (−) 102 ± 19 |
| AC10065 | 1.4 ± 0.2 | 99 ± 0.5 | 4.1 ± 0.4 | 89 ± 2 | (−) 235 ± 41 | (−) 158 ± 43 |
| AC10066 | 2.8 ± 0.6 | 97 ± 1 | 7.5 ± 1 | 90 ± 10 | (−) 204 ± 30 | (−) 140 ± 16 |
| AC10067 | 4.6 ± 2 | 93 ± 5 | 9 ± 5 | 75 ± 12 | (−) 182 ± 39 | (−) 157 ± 33 |
| AC10068 | 5 ± 1 | 97 ± 1 | 6 ± 1 | 80 ± 9 | (−) 191 ± 31 | (−) 227 ± 72 |
| AC10069 | 9.6 ± 1 | 96 ± 1 | 15 ± 2 | 83 ± 7 | (−)136 ± 21 | (−)330 ± 67 |
| AC10070 | 4.8 ± 1 | 90 ± 2 | 9 ± 1 | 79 ± 11 | (−)180 ± 15 | (−)203 ± 35 |
| AC10071 | 3.7 ± 1 | 100 ± 1 | 7 ± 1 | 83 ± 7 | (−)341 ± 52 | (−) 279 ± 56 |
| AC10072 | 9.1 ± 3 | 85 ± 4 | 2.4 ± 0.02 | 78 ± 13 | (−)89 ± 18 | (−)93 ± 9 |
| AC10073 | 26 ± 11 | 64 ± 8 | 13 ± 2 | 65 ± 12 | (−)137 ± 36 | (−)103 ± 20 |
| AC10074 | 9.4 ± 1 | 85 ± 3 | 10 ± 0.4 | 79 ± 6 | (−)42 ± 14 | (−)18 ± 14 |

Experimental Methods

Compounds and Other Chemicals Used.

Forskolin and phorbol 12-myristate 13-acetate (PMA) were purchased from Tocris (Ellisville, Mo.). 4-(2-hydroxyethyl)-1-piperazineethanesulfonic acid (HEPES), and ethylenediaminetetraacetic acid (EDTA) were purchased from Fisher Scientific (Pittsburgh, Pa.). NKY80 was purchased from EMD Millipore (Temecula, Calif.). Isoproterenol, A23187, adenosine monophosphate (ATP), ethyleneglycol-bis(2-aminoethylether)-N,N,N',N'-tetra acetic acid (EGTA), 3-isobutyl-1-methylxanthine (IBMX), 5'-guanylyl-imidodiphosphoate (GppNHp), TWEEN 20, $MgCl_2$, and 2-amino-2-(hydroxymethyl)-1,3-propanediol (TRIS) were purchased from Sigma-Aldrich (St. Louis, Mo.). 2-Bromo-1-(1-phenyl-4,5-dihydro-1H-benzo[d]azepin-3(2H)-yl)ethanone (W400), 6-chloro-2-(trichloromethyl)-4H-chromen-4-one (ST034307), and 4-chloro-1-methyl-3-nitroquinolin-2(1H)-one (ST072383) were purchased from TimTec (Newark, Del.).

Cell Culture.

Human embryonic kidney (HEK) cells stably expressing AC1, AC8, or AC1 with the MOR were cultured in Dulbecco's Modified Eagle Medium (Life Technologies, Grand Island, N.Y.) supplemented with 5% bovine calf serum (Hyclone, Logan, Utah), 5% fetal clone I (Hyclone), Antibiotic-Antimycotic (Life Technologies), and G418 (Invivogen, San Diego, Calif.) (HEK-AC1), or hygromycin B (Fisher Scientific, Pittsburgh, Pa.) (HEK-AC8), or G418 and puromycin (Sigma-Aldrich) (HEK-AC1/MOR). Chinese hamster ovary (CHO) cells expressing the MOR (CHO-MOR) in the PathHunter® β-Arrestin GPCR assay platform were purchased from DiscoveRx (Freemont, Calif.). Cells were grown in Ham's F12 media supplemented with 1 mM L-glutamine (Thermo Scientific, West Palm Beach, Fla.), 10% fetal bovine serum (Hyclone), 50 U/ml penicillin, 50 μg/ml streptomycin (Life Technologies), G418 and hygromycin B. Cells were grown and frozen as previously described (J. M. Conley, et al., *J Vis Exp*, e51218 (2014)).

Transient Transfections.

HEK cells were plated in 15 cm dishes at a confluence of $9.0 \times 10^6$ cells/dish and incubated at 37° C. in a humidified incubator overnight. On the following day, a 6 ml solution containing 9 μg of AC plasmid or venus fluorescent protein (venus) control plasmid, and 60 μL lipofectamine 2000 (Life Technologies) in optiMEM (Life Technologies) was prepared and incubated at room temperature for 45 min. The solution was added dropwise to the cells, and transfection was carried out for 48 h. Cells were harvested, and cryopreserved as described above. For AC7 and AC9, HEK cells were plated in 10 cm dishes (at confluences of $3.0 \times 10^6$ or $3.5 \times 10^6$ cells/dish, respectively) and incubated at 37° C. in a humidified incubator overnight. On the following day, a 3 mL solution containing AC7 plasmid (10 µg), AC9 plasmid (3 µg), or venus plasmid; plus Gas plasmid (0.5 µg for AC7 and 0.3 µg for AC9) or venus plasmid; and Lipofectamine 2000 (48 µL for AC7 and 24 µl for AC9) in optiMEM was prepared and incubated at room temperature for 45 min. The solution was added dropwise to the cells, transfection was carried out for 48 h, and cells were harvested and cryopreserved.

Cyclic AMP Accumulation in Cells.

Cyclic AMP accumulation was measured as previously described (Brust, et al., *J. Pharmacol. Exp. Ther.* 352, 480-493(2015)). Briefly, cryopreserved cells were thawed, resuspended in optiMEM (Life Technologies), and plated in white, flat bottom, low-volume, tissue culture-treated 384 well plates (PerkinElmer, Shelton, Conn.). Plates with cells were incubated in a 37° C. humidified incubator for 1 h. Inhibitors were added and plates were incubated at room temperature for 30 min followed by the addition of AC stimulants in the presence of 500 µM IBMX. Cells were incubated at room temperature for 1 h and cAMP accumulation was measured using Cisbio's cAMP kit (Cisbio Bioassays, Bedford, Mass.) according to the manufacturer's instructions.

Additional assays measured cAMP accumulation using the HitHunter® cAMP Assay Platform from DiscoveRx according to the manufacturer's instructions. Luminescence (HitHunter® cAMP Assay) and fluorescence (Cisbio's dynamic 2 kit) counts were measured using a Synergy 4 (BioTek, Winooski, Vt.).

Compound Screening.

Cryopreserved HEK-AC1 cells were thawed, washed, resuspended in optiMEM and plated into white, flat bottom, tissue culture-treated 384-well plates (PerkinElmer) at 15 µL/well using a MultiFlo dispenser (BioTek). Cells were incubated in a 37° C. humidified incubator for 1 h. Next, test compounds (3.5 mg/l final assay concentration) from the NDL-3000 Natural Derivatives library (TimTec) were added (70 nL/well) using a MultiPette-mounted 384 well pin tool and incubated at room temperature for 30 min. Following the incubation with test compounds, 5 µL/well of 3 µM A23187 in the presence of 30 nM forskolin and 500 µM IBMX (final concentrations) was added to the cells using a MultiFlo dispenser. Cells were incubated at room temperature for 1 h and cAMP accumulation was measured as described above using a MultiFlo dispenser to sequentially add 10 µL/well of cAMP-d2 and anti-cAMP cryptate conjugate working solutions (Cisbio Bioassays) to the cells. Test compounds were screened in singlet and a Z' factor of 0.55±0.22 (n=10) was obtained using 30 µM W400 as a positive control (J. M. Conley, et al., *J. Pharmacol. Exp. Ther.* 347, 276-287 (2013); J.-H. Zhang, *J. Biomol. Screen.* 4, 67-73 (1999).

Cell Viability Assays.

Cell viability assays were conducted with HEK-AC1 cells following plating and compound incubation protocols identical to the procedures described above in "Cyclic AMP assays in cells". Cell viability was measured as a percentage of vehicle using 2% Triton X-100 (Sigma-Aldrich) as a control. The CellTiter-Glo® Luminescent Cell Viability Assay kit from Promega (Madison, Wis.) was employed to assess cell viability according to the manufacturer's instructions. Luminescence counts were measured using a Synergy 4.

Cyclic AMP Accumulation in Cellular Membranes from HEK Cells.

Cellular membranes from HEK-AC1 cells were isolated and frozen as previously described in the presence of 1 mM EGTA (T. F. Brust, et al., *J. Pharmacol. Exp. Ther.* 352, 480-493 (2015). On the assay day membranes were thawed on ice and resuspended in membrane buffer (33 mM HEPES, 0.1% TWEEN 20, 1 mM EGTA, pH 7.4). Protein concentration was measured using the Pierce BCA Protein Assay kit (Thermo Scientific) and 2.0-3.5 µg/well was plated in a white, flat bottom, tissue culture-treated 384 well plate. Inhibitors (diluted in a 33 mM HEPES, 0.1% TWEEN 20 solution) were added and incubated for 20 min at room temperature. Next, 3 µM calmodulin or 30 µM forskolin (final concentrations) was added in stimulation buffer (33 mM HEPES, 0.1% TWEEN 20, 1.5 mM $MgCl_2$, 250 µM ATP, 1 M GppNHp, 500 µM IBMX, and 500 µM $CaCl_2$-10 M free $Ca^{2+}$) and incubated at room temperature for 45 min. Cyclic AMP accumulation was measured using Cisbio's dynamic 2 kit according to the manufacturer's instructions.

Adenylyl Cyclase Assays in Cellular Membranes from Sf9 Cells.

Membranes from Sf9 cells expressing AC1, AC2, or AC5 were prepared as previously described (C. W. Dessauer, *Methods Enzymol.* 345, 112-126 (2002)). All activity assays were performed for 10 min at 30° C. in a final volume of 50 µL. The final concentration of $MgCl_2$ and Mg-ATP in the reaction was 10 mM and 200 µM, respectively. AC-containing membranes (10-20 µg) were premixed with $G\alpha_s$ (50 nM final). Inhibitors were solubilized in DMSO and incubated with AC-containing membranes for 10 min on ice before the start of the reaction. The final concentration of DMSO in the reaction did not exceed 3% for either vehicle or inhibitors. Reactions were initiated upon addition of a reaction mix containing $[\alpha\text{-}^{32}P]ATP$. The reactions were terminated with stop solution (2.5% SDS, 50 mM ATP, and 1.75 mM cAMP) and the products were separated by sequential chromatography on Dowex-50 and $Al_2O_3$.

Assays with Hippocampal Homogenates.

C57BL/6 mice (13 weeks old) were decapitated, their brains were quickly removed, and 2-mm slices encompassing the hippocampus were collected on ice. The hippocampal region was dissected and immediately frozen in a −80° C. freezer, where they were stored until the assay day. Dissected hippocampal tissue was thawed on ice, weighed, and homogenized in membrane buffer (2 mL/mg—wet weight) with ten manual strokes using a Wheaton-Teflon glass homogenizer. Homogenates were added to a white, flat bottom, tissue culture-treated 384-well plate and inhibitors (diluted in a 33 mM HEPES, 0.1% TWEEN 20 solution) were added and incubated for 20 min at room temperature. Next, 3 µM calmodulin (final concentration) was added in stimulation buffer (same as assays in cellular membranes from HEK cells) and incubated at room temperature for 45 min. Cyclic AMP accumulation was measured using Cisbio's dynamic 2 kit according to the manufacturer's instructions.

β-Arrestin Recruitment Assay.

Recruitment of β-arrestin 2 to the MOR was measured as previously described (T. F. Brust, et al., *J. Pharmacol. Exp. Ther.* 352, 480-493 (2015)). Briefly, CHO-MOR cells were plated in white, flat bottom, low-volume, tissue culture-treated 384-well plates. Plates with cells were incubated in a 37° C. humidified incubator overnight. Following the incubation, AC1 inhibitors or vehicle was added to the cells, which were incubated at room temperature for 30 min. Next, DAMGO or vehicle was added to cells, which were then incubated in a 37° C. humidified incubator for 1.5 h. β-arrestin 2 recruitment to the MOR was assessed using the PathHunter® assay (DiscoveRx) according to the manufacturer's instructions. Luminescence counts were measured using a Synergy 4.

Heterologous Sensitization Assays.

Heterologous sensitization assays were conducted as previously described (T. F. Brust, et al., *Biochem. Pharmacol.* 93, 85-91 (2015)). Briefly, HEK-AC1/MOR cells were thawed and plated in white, flat bottom, tissue culture-treated 384-well plates. Plates with cells were incubated in a 37° C. humidified incubator for 1 h. For inhibition of the development of sensitization, inhibitors were added and plates were incubated at room temperature for 30 min, followed by addition of DAMGO and incubation at 37° C. for 2 h (to achieve sensitization). For the assays to measure inhibition of the expression of sensitization the order of DAMGO and ST034307 additions were reversed (i.e., DAMGO sensitization before AC1 inhibition). Next, cells were treated with 3 M A23187 in the presence of 500 μM IBMX and 1 M naloxone (final concentrations) and incubated at room temperature for 1 h. Cyclic AMP accumulation was measured using Cisbio's dynamic 2 kit according to the manufacturer's instructions.

Animals and Housing.

Wild-type C57BL/6 mice, were obtained from Taconic (Cambridge City, Ind.). Male mice age 5 weeks (18-23 gr) were grouped and housed in single grommet ventilated plexiglass cages at ambient temperature (21° C.) in a room maintained on a reversed 12L:12D cycle (lights off at 10:00, lights on at 22:00) in our animal facility that has Association for Assessment and Accreditation of Laboratory Animal Care approval. Food and water were provided ad libitum. The mice were given ~7 days to acclimatize to the housing conditions and reverse light cycle before the start of the experiments. Mice were then habituated to the containment boxes for the Von Frey assay. All animal procedures were pre-approved by our Institutional Animal Care and Use Committee and were in accordance with the National Institutes of Health *Guide for the Care and Use of Laboratory Animals*. Mice were not deprived of food or water at any time.

Inflammatory Pain Behavioral Assays.

C57BL/6 mice were placed in suspended rectangular plastic chambers on a wire mesh grid to habituate for 1 h. Next, a baseline measurement of mechanical sensitivity to Von Frey filaments was performed as previously described (G. Corder, et al., *Science* 341, 1394-1399 (2013); R. M. van Rijn, et al., *Biol. Psychiatry* 71, 232-238 (2012)). Immediately after baseline measurements, the mice were injected with Complete Freund's adjuvant (CFA—10 μL, non-diluted) into the intraplantar surface of the left hindpaw to induce inflammation. On the following day, inflammatory hypersensitivity was measured using Von Frey filaments. Next, drugs were injected intrathecally as previously described (T. F. Brust, et al., *Biochem. Pharmacol.* 93, 85-91 (2015); R. M. van Rijn, et al., *Biol. Psychiatry* 71, 232-238 (2012)). Drug-induced analgesia was measured 10 min after intrathecal injections using Von Frey filaments. Data are represented as a percentage of the average baseline response.

Data and Statistical Analyses.

All data and statistical analyses were carried out using GraphPad Prism 6 (GraphPad Software, San Diego, Calif.). Statistical analyses (one-way ANOVA or t tests) are described in text or figure legends where appropriate.

Synthetic Chemistry.

The purity of all final compounds was >95% purity as assessed by HPLC according to current American Chemical Society guidelines for publication. Final compounds were analyzed on an Agilent 1200 series chromatograph. The chromatographic method utilized as Thermo Scientific Hypersil GOLD C-18 4.6×250 mm, 3 μm column. UV detection wavelength=220 nm; flow-rate=1.0 mL/min; gradient=5-95% acetonitrile over 12 min and 3 min hold time at 95% acetonitrile. Both organic and aqueous mobile phases contain 0.1% v/v formic acid. The mass spectrometer used is an AB Sciex 4500 QTrap triple-quadrupole mass spectrometer with an ESI source. Samples are submitted for analysis solubilized in 1:1 acetonitrile:water solution. $^1$H and $^{13}$C NMR spectra were recorded on either Bruker DRX500 spectrometer (operating at 500 and 125 MHz, respectively) or Bruker AVIII (operating at 800 and 200 MHz, respectively) in DMSO-$d_6$ or CDCl$_3$ with or without the internal standard of TMS at 0.05% v/v. The chemical shifts (δ) reported as parts per million (ppm) and the coupling constants are reported as s=singlet, bs=broad singlet, d=doublet, t=triplet, q=quartet, dd=doublet of doublet, m=multiplet. Compounds were generally prepared according to scheme 1 and protocols are detailed below.

Scheme 1. Chemical Synthesis for 1,3,4-oxadiazole series of AC1 inhibitors

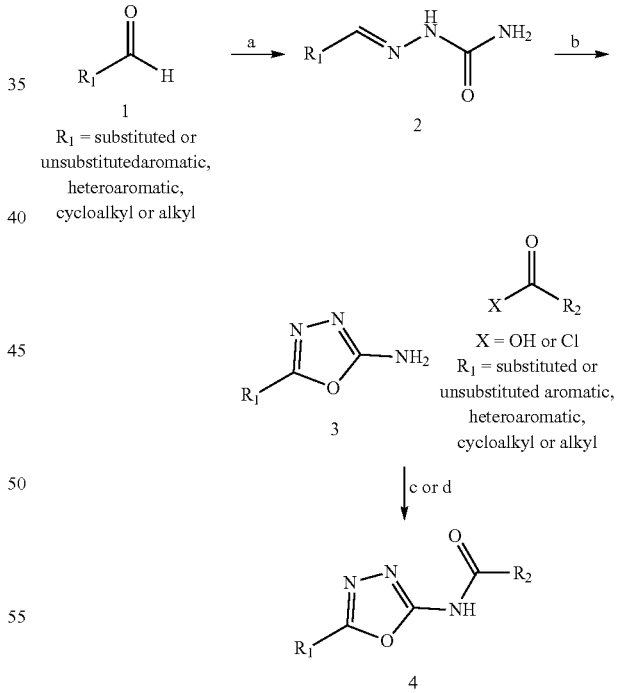

Reagents: (a) hydrazine carboxamide HCl, sodium acetate, methanol, water, rt, 30-60 min, 86-98%; (b) sodium acetate, bromine, acetic acid, 60° C., 2 h, 70-95%; (c) if X = OH: oxalyl chloride, DMF, DCM, 0° C.-rt, 1 h, crude product carried into next step; (d) if X = Cl: pyridine, rt, 16 h, 2-77%.

The following procedure was carried out for all analogs and is detailed for compound 10 (AC10007). All other analogs followed this protocol unless otherwise noted.

Synthesis of 4-bromo-N-(5-cyclohexyl-1,3,4-oxadiazol-2-yl)benzamide (10, AC10007)

Step 1:

To a vial was added the hydrazinecarboxamide hydrochloride (0.78 g, 7.0 mmol, 1.0 eq.) and sodium acetate (1.15 g, 14.0 mmol, 2.0 eq.) followed by water (10 mL). To a second vial was added the cyclohexanecarbaldehyde (0.787 g, 0.85 mL, 7.02 mmol, 1.0 eq.) and methanol (10 mL). The aldehyde solution was then added dropwise to the first solution while stirring at rt. The reaction stirred for 30 min in which time it formed a suspension. The solid was filtered out by vacuum filtration to produce the desired product (E)-2-(cyclohexylmethylene) hydrazine-1-carboxamide (1.06 g, 6.26 mmol, 89%) as a white solid. $^1$H NMR (500 MHz, DMSO-$d_6$): δ 9.72 (s, 1H), 7.06 (d, J=5.2 Hz, 1H), 6.08 (s, 2H), 2.18-2.05 (m, 1H), 1.76-1.66 (m, 4H), 1.65-1.57 (m, 1H), 1.33-1.12 (m, 5H).

Step 2:

To a vial was added the (E)-2-(cyclohexylmethylene) hydrazine-1-carboxamide (0.18 g, 1.1 mmol, 1.0 eq.), sodium acetate (0.17 g, 2.1 mmol, 2.0 eq.) and acetic acid (0.5 mL). To a second vial was added the bromine (0.060 mL, 1.2 mmol, 1.1 eq.) in acetic acid (0.5 mL). The bromine solution was then added to the first vial while stirring in a dropwise manner at rt. The reaction was then heated to 60° C. and stirred for 1 h. The reaction was then cooled to rt and poured onto ice water. A precipitate formed and was filtered by vacuum filtration then rinsed with DCM to provide pure product 5-cyclohexyl-1,3,4-oxadiazol-2-amine (0.15 g, 0.87 mmol, 83%) as a pale yellow solid. $^1$H NMR (500 MHz, DMSO-$d_6$): δ 6.82 (s, 2H), 2.71 (tt, J=10.9, 3.6 Hz, 1H), 1.95-1.87 (m, 2H), 1.75-1.68 (m, 2H), 1.67-1.58 (m, 1H), 1.48-1.29 (m, 4H), 1.28-1.20 (m, 1H).

Step 3: (Procedure Includes Converting Carboxylic Acid to Acyl Chloride. If the Acyl Chloride is Commercially Available then the Oxalyl Chloride Step can be Bypassed):

To a vial was added the 4-bromobenzoic acid (0.033 g, 0.16 mmol, 1.1 eq.) in DCM (0.5 mL) followed by 1 drop of DMF. The reaction was then cooled to 0° C. followed by slow addition of oxalyl chloride (0.016 mL, 0.18 mmol, 1.15 eq.). The reaction then was allowed to warm to rt and stir for 1 hour. After 1 hour the reaction was concentrated in vacuo and carried into the amide coupling reaction without purification or characterization.

To a second vial was added the 5-cyclohexyl-1,3,4-oxadiazol-2-amine (0.025 g, 0.15 mmol, 1.0 eq.) followed by pyridine (0.3 mL). To a second vial was added the 4-bromobenzoyl chloride (carried over from previous step) and this was suspended in pyridine (0.3 mL). The acyl chloride was added to the first vial while stirring at rt. The reaction stirred at rt overnight. The reaction was then poured into ice water and a precipitate formed. This precipitate was filtered by vacuum filtration and was further purified by reverse-phase flash chromatography (5-100% MeCN:water, 20 min.). All fractions were analyzed for purity by HPLC and the fractions that met >95% purity threshold were pooled and concentrated to produce the desired product 4-bromo-N-(5-cyclohexyl-1,3,4-oxadiazol-2-yl)benzamide (0.041 g, 0.12 mmol, 77%) as a white solid. $^1$H NMR (500 MHz, DMSO-$d_6$): δ 12.06-11.91 (m, 1H), 7.93 (d, J=8.0 Hz, 2H), 7.80 (d, J=8.0 Hz, 2H), 2.95 (s, 1H), 2.01 (dt, J=13.3, 3.9 Hz, 2H), 1.75 (dp, J=11.9, 3.9 Hz, 2H), 1.65 (dt, J=12.8, 4.0 Hz, 1H), 1.59-1.49 (m, 2H), 1.40 (qt, J=11.9, 3.4 Hz, 2H), 1.28 (m, 1H). $^{13}$C NMR (200 MHz, DMSO-$d_6$): δ 167.4, 164.6, 157.7, 150.0, 132.1, 130.7, 127.3, 34.6, 29.9, 25.6, 25.0. ESI-MS: m/z 349.9 [M+], 351.9 [M+2]; HPLC retention time: 12.760 min. HPLC purity 98%.

N-(5-(2,3-dihydrobenzo[b][1,4]dioxin-6-yl)-1,3,4-oxadiazol-2-yl)benzamide (4, AC10001)

Isolated as a white solid (0.032 g, 0.099 mmol, 42%). $^1$H NMR (500 MHz, DMSO-$d_6$): δ 12.22 (s, 1H), 8.05 (d, J=7.6 Hz, 2H), 7.63 (t, J=7.4 Hz, 1H), 7.54 (t, J=7.6 Hz, 2H), 7.44 (dd, J=8.4, 2.1 Hz, 1H), 7.39 (d, J=2.0 Hz, 1H), 7.08 (d, J=8.4 Hz, 1H), 4.34 (q, J=5.6 Hz, 4H). $^{13}$C NMR (200 MHz, DMSO-$d_6$): δ 146.3, 143.8, 132.3, 128.4, 128.3, 119.4, 118.1, 116.7, 114.5, 64.4, 64.1. ESI-MS: m/z 323.6 [M+]; HPLC retention time: 11.191 min. HPLC purity 99.6%.

N-(5-(5,6,7,8-tetrahydronaphthalen-2-yl)benzamide (5, AC10002)

Isolated as a pale yellow solid (0.028 g, 0.084 mmol, 40%). $^1$H NMR (500 MHz, CDCl$_3$): δ 12.21 (br s, 1H), 8.26 (d, J=7.7 Hz, 2H), 7.84-7.74 (m, 2H), 7.62 (t, J=7.3 Hz, 1H), 7.53 (t, J=7.5 Hz, 2H), 7.19 (d, J=7.8 Hz, 1H), 2.89-2.79 (m, 4H), 1.89-1.79 (m, 4H). $^{13}$C NMR (200 MHz, DMSO-$d_6$): δ 165.0, 161.5, 157.7, 141.1, 137.9, 132.9, 132.2, 130.0, 128.6, 128.3, 126.5, 123.1, 120.5, 28.84, 28.58, 22.35, 22.30. ESI-MS: m/z 319.7 [M+]; HPLC retention time: 12.940 min. HPLC purity 96.5%.

N-(5-cyclohexyl-1,3,4-oxadiazol-2-yl)benzamide (6, AC10003)

Isolated as an off-white solid (0.035 g, 0.125 mmol, 40%). $^1$H NMR (800 MHz, DMSO-$d_6$) δ 11.87 (br s, 1H), 8.01 (d, J=7.6 Hz, 2H), 7.65 (t, J=7.4 Hz, 1H), 7.55 (t, J=7.6 Hz, 2H), 2.98-2.91 (m, 1H), 2.04-1.99 (m, 2H), 1.75 (dt, J=13.4, 4.0 Hz, 2H), 1.65 (dt, J=13.0, 4.0 Hz, 1H), 1.54 (qd, J=11.6, 3.5 Hz, 2H), 1.39 (qt, J=11.9, 3.6 Hz, 2H), 1.28 (qt, J=11.9, 3.6 Hz, 1H). $^{13}$C NMR (200 MHz, DMSO-$d_6$): δ 166.84, 165.11, 157.47, 132.77, 132.30, 128.58, 128.22, 34.15, 29.41, 25.16, 24.60. ESI-MS: m/z 271.7 [M+]; HPLC retention time: 11.721 min. HPLC purity 95.1%.

N-(5-(4-fluorophenyl)-1,3,4-oxadiazol-2-yl)benzamide (7, AC10004)

Isolated as pink solid (0.026 g, 0.091 mmol, 66%). $^1$H NMR (800 MHz, DMSO-$d_6$) δ 12.17 (s, 1H), 8.08-8.00 (m, 4H), 7.68 (t, J=7.4 Hz, 1H), 7.58 (t, J=7.7 Hz, 2H), 7.47 (t, J=8.8 Hz, 2H). $^{13}$C NMR (200 MHz, DMSO-$d_6$): δ 165.0, 163.9 (d, J=250.0 Hz) 160.5, 158.0, 132.9, 132.2, 128.7 (d, J=9.2 Hz), 128.6, 128.3, 120.1, 116.7 (d, J=22.4 Hz). ESI-MS: m/z 283.6 [M+], 306.0 [M+Na]; HPLC retention time: 11.428 min. HPLC purity 97.4%.

4-bromo-N-(5-(5,6,7,8-tetrahydronaphthalen-2-yl)-1,3,4-oxadiazol-2-yl)benzamide (8, AC10005)

Isolated as light pink solid (0.049 g, 0.117 mmol, 50%). $^1$H NMR (800 MHz, DMSO-$d_6$) δ 12.04 (s, 1H), 8.12 (d, J=8.5 Hz, 2H), 7.78-7.71 (m, 2H), 7.70-7.59 (m, 2H), 7.21 (d, J=8.1 Hz, 1H), 2.89-2.78 (m, 4H). HPLC retention time: 13.657 min. HPLC purity 95.3%.

N-(5-(thiophen-2-yl)-1,3,4-oxadiazol-2-yl)benzamide (9, AC10006)

Isolated as white solid (0.055 g, 0.199 mmol, 60%) $^1$H NMR (800 MHz, DMSO-$d_6$) δ 12.17 (s, 1H), 8.05 (d, J=7.7

Hz, 2H), 7.94 (d, J=4.9 Hz, 1H), 7.78 (d, J=3.7 Hz, 1H), 7.67 (t, J=7.4 Hz, 1H), 7.57 (t, J=7.6 Hz, 2H), 7.30 (dd, J=5.0, 3.6 Hz, 1H). $^{13}$C NMR (200 MHz, DMSO-d$_6$): δ 165.0, 157.5, 157.4, 132.9, 132.2, 131.1, 129.7, 128.7, 128.6, 128.3, 124.3. ESI-MS: m/z 271.6 [M+]; HPLC retention time: 10.957 min. HPLC purity 98.4%.

4-bromo-N-(5-(4-fluorophenyl)-1,3,4-oxadiazol-2-yl)benzamide (11, AC10008)

Isolated as light pink solid (0.038 g, 0.17 mmol, 61%). $^1$H NMR (800 MHz, DMSO-d$_6$) δ 12.28 (s, 1H), 8.06-8.01 (m, 2H), 7.98 (d, J=8.1 Hz, 2H), 7.80 (d, J=8.1 Hz, 2H), 7.50-7.44 (m, 2H). $^{13}$C NMR (200 MHz, DMSO-d$_6$): δ 164.2, 164.0 (d, J=249.7 Hz), 160.5, 157.8, 131.7, 131.4, 130.4, 128.8 (d, J=9.1 Hz), 126.9, 120.0, 116.3 (d, J=22.5 Hz). ESI-MS: m/z 361.9 [M+], 363.9 [M+2]. HPLC retention time: 12.377 min. HPLC purity 97.1%.

4-Bromo-N-(5-(thiophen-2-yl)-1,3,4-oxadiazol-2-yl)benzamide (12, AC10009)

Isolated as white solid (0.055 g, 0.199 mmol, 60%). $^1$H NMR (800 MHz, DMSO-d$_6$) δ 12.23 (s, 1H), 7.98-7.91 (m, 3H), 7.80-7.74 (m, 3H), 7.28 (dd, 1H). $^{13}$C NMR (200 MHz, DMSO-d$_6$): δ 164.55, 158.07, 157.58, 132.17, 131.65, 130.82, 130.16, 129.19, 127.39, 124.69. ESI-MS: m/z 349.9 [M+], 351.9 [M+2]; HPLC retention time: 11.964 min. HPLC purity 97.6%.

4-isopropoxy-N-(5-(5,6,7,8-tetrahydronaphthalen-2-yl)-1,3,4-oxadiazol-2-yl)benzamide (13, AC10010)

Isolated as white solid (0.010 g, 0.027 mmol, 12%). $^1$H NMR (800 MHz, DMSO-d$_6$) δ 8.00-7.98 (m, 2H), 7.66-7.64 (m, 1H), 7.64-7.62 (m, 1H), 7.27-7.24 (m, 1H), 7.05-7.03 (m, 2H), 4.75 (p, J=6.0 Hz, 1H), 2.82-2.75 (m, 4H), 1.77-1.73 (m, 4H), 1.29 (d, J=6.0 Hz, 6H). $^{13}$C NMR (200 MHz, DMSO-d$_6$): δ 165.22, 161.65, 158.69, 141.41, 138.34, 130.94, 130.45, 126.86, 124.64, 123.49, 121.11, 115.51, 70.10, 29.30, 29.06, 22.82, 22.78, 22.16. ESI-MS: m/z 378.0 [M+]; HPLC retention time: 13.579 min. HPLC purity 98.1%.

N-(5-cyclohexyl-1,3,4-oxadiazol-2-yl)-3-(methylthio)benzamide (14, AC10011)

Isolated as white solid (0.013 g, 0.040 mmol, 23%). $^1$H NMR (800 MHz, DMSO-d$_6$) δ 11.91 (s, 1H), 7.84 (s, 1H), 7.75-7.72 (m, 1H), 7.54-7.50 (m, 1H), 7.47 (t, J=7.8 Hz, 1H), 2.94 (tt, J=11.1, 3.9 Hz, 1H), 2.55 (s, 3H), 2.02-1.96 (m, 2H), 1.74 (dt, J=13.3, 4.0 Hz, 2H), 1.65 (dt, J=12.9, 4.0 Hz, 1H), 1.57-1.50 (m, 2H), 1.43-1.33 (m, 2H), 1.31-1.23 (m, 1H). $^{13}$C NMR (200 MHz, DMSO-d$_6$): δ 167.3, 165.1, 157.9, 139.6, 133.5, 130.4, 129.6, 125.4, 125.1, 34.6, 29.9, 25.6, 25.1, 15.0. ESI-MS: m/z 317.7 [M+]; HPLC retention time: 12.531 min. HPLC purity 98.9%.

3-(methylthio)-N-(5-(thiophen-2-yl)-1,3,4-oxadiazol-2-yl)benzamide (15, AC10012)

Isolated as white solid (0.006 g, 0.016 mmol, 12%). $^1$H NMR (800 MHz, DMSO-d$_6$) δ 12.19 (s, 1H), 7.94 (dd, J=5.0, 1.2 Hz, 1H), 7.87 (s, 1H), 7.79-7.76 (m, 2H), 7.54 (t, J=7.7 Hz, 1H), 7.50 (t, J=7.7 Hz, 1H), 7.30 (dd, J=5.0, 3.7 Hz, 1H), 2.56 (s, 3H). $^{13}$C NMR (200 MHz, DMSO-d$_6$): δ 164.46, 157.54, 157.24, 139.19, 132.86, 131.14, 130.03, 129.65, 129.16, 128.72, 124.94, 124.71, 124.28, 14.50. ESI-MS: m/z 317.7 [M+], 340.0 [M+Na]; HPLC retention time: 11.811 min. HPLC purity 97.3%.

3-(methylthio)-N-(5-(5,6,7,8-tetrahydronaphthalen-2-yl)-1,3,4-oxadiazol-2-yl)benzamide (16, AC10013)

Isolated as white solid (0.015 g, 0.047 mmol, 26%). $^1$H NMR (800 MHz, CDCl$_3$) δ 8.07 (s, 1H), 7.97 (d, J=7.7 Hz, 1H), 7.79 (s, 2H), 7.53-7.41 (m, 2H), 7.20 (d, J=8.4 Hz, 1H), 2.89-2.82 (m, 4H), 2.55 (s, 3H), 1.88-179 (m, 4H). $^{13}$C NMR (200 MHz, CDCl$_3$) δ 141.98, 139.92, 138.17, 130.82, 129.87, 128.99, 127.32, 126.19, 125.26, 123.67, 120.20, 29.60, 29.26, 22.85, 22.78, 15.61. ESI-MS: m/z 366.0 [M+], 388.0 [M+Na]; HPLC retention time: 13.511 min. HPLC purity 95.8%.

N-(5-(furan-2-yl)-1,3,4-oxadiazol-2-yl)benzamide (17, AC10014)

Isolated as white solid (0.032 g, 0.125 mmol, 38%). $^1$H NMR (800 MHz, CDCl$_3$) δ 11.73 (s, 1H), 8.20 (d, J=7.6 Hz, 2H), 7.71-7.60 (m, 2H), 7.59-7.47 (m, 2H), 7.21 (d, J=3.5 Hz, 1H), 6.64-6.59 (m, 1H). $^{13}$C NMR (200 MHz, CDCl$_3$) δ 165.4, 157.7, 154.7, 147.2, 138.9, 133.4, 132.5, 129.2, 129.1, 129.0, 128.8, 114.3, 113.0. ESI-MS: m/z 255.6 [M+], 278.0 [M+Na]; HPLC retention time: 10.424 min. HPLC purity 95.8%.

4-bromo-N-(5-(2,3-dihydrobenzo[b][1,4]dioxin-6-yl)-1,3,4-oxadiazol-2-yl)benzamide (18, AC10015)

Isolated as white solid (0.002 g, 0.005 mmol, 2%). $^1$H NMR (800 MHz, DMSO-d$_6$) δ 12.27 (s, –1H), 7.97 (d, J=8.1 Hz, 1H), 7.74 (d, J=8.1 Hz, 2H), 7.42 (dd, J=8.4, 2.1 Hz, 1H), 7.36 (d, J=2.1 Hz, 1H), 7.06 (d, J=8.4 Hz, 1H), 4.37-4.24 (m, 4H). $^{13}$C NMR (200 MHz, DMSO-d$_6$) δ 146.8, 144.3, 132.0, 131.2, 130.9, 126.8, 119.9, 118.6, 117.0, 115.0, 64.9, 64.6. ESI-MS: m/z 401.8 [M+], 403.8 [M+2]; HPLC retention time: 12.191 min. HPLC purity 96.7%.

3-methoxy-N-(5-(5,6,7,8-tetrahydronaphthalen-2-yl)-1,3,4-oxadiazol-2-yl)benzamide (19, AC10016)

Isolated as white solid (0.031 g, 0.088 mmol, 39%). $^1$H NMR (800 MHz, DMSO-d$_6$) δ 12.11 (s, 1H), 7.76-7.53 (m, 4H), 7.46 (t, J=7.9 Hz, 1H), 7.30-7.15 (m, 2H), 3.83 (s, 3H), 2.83-2.68 (m, 4H), 1.81-1.61 (m, 4H). $^{13}$C NMR (200 MHz, DMSO-d$_6$) δ 165.42, 161.60, 159.70, 158.25, 141.51, 138.35, 134.17, 130.44, 130.24, 126.90, 123.52, 121.02, 120.99, 119.41, 113.51, 55.85, 29.30, 29.05, 22.81, 22.76. ESI-MS: m/z 350.1 [M+H], 372.1 [M+Na]; HPLC retention time: 13.034 min. HPLC purity 95.2%.

4-isopropoxy-N-(5-(thiophen-2-yl)-1,3,4-oxadiazol-2-yl)benzamide (20, AC10017)

Isolated as white solid (0.058 g, 0.174 mmol, 59%). $^1$H NMR (800 MHz, DMSO-d$_6$) δ 11.91 (br s, 1H), 7.99 (d, J=8.4 Hz, 2H), 7.92-7.90 (m, 1H), 7.75-7.73 (m, 1H), 7.28-7.26 (m, 1H), 7.04 (d, J=8.5 Hz, 2H), 4.74 (p, J=6.0 Hz, 1H), 1.28 (d, J=6.1 Hz, 6H). $^{13}$C NMR (200 MHz, DMSO-d$_6$) δ 164.7, 161.8, 158.1, 157.9, 131.5, 131.0, 130.0, 129.1, 124.8, 124.1, 115.6, 70.1, 22.1. ESI-MS: m/z 330.1 [M+H], 352.2 [M+Na]; HPLC retention time: 12.019 min. HPLC purity 98.7%.

4-methoxy-N-(5-(thiophen-2-yl)-1,3,4-oxadiazol-2-yl)benzamide (21, AC10018)

Isolated as white solid (0.014 g, 0.046 mmol, 27%). $^1$H NMR (800 MHz, DMSO-$d_6$) δ 11.94 (br s, 1H), 8.03 (d, J=8.8 Hz, 2H), 7.93 (dd, J=5.0, 1.2 Hz, 1H), 7.76 (dd, J=3.6, 1.2 Hz, 1H), 7.29 (dd, J=5.0, 3.7 Hz, 1H), 7.09 (d, J=8.8 Hz, 2H), 3.86 (s, 3H). $^{13}$C NMR (200 MHz, DMSO-$d_6$) δ 164.3, 163.0, 157.6, 131.1, 130.5, 129.6, 128.7, 124.4, 124.2, 113.9, 55.6, 39.5. ESI-MS: m/z 301.6 [M+H], HPLC retention time: 11.009 min. HPLC purity 97.0%.

4-isopropoxy-N-(5-(furan-2-yl)-1,3,4-oxadiazol-2-yl)benzamide (22, AC10019)

Isolated as white solid (0.010 g, 0.032 mmol, 18%). $^1$H NMR (800 MHz, DMSO-$d_6$) δ 11.94 (br s, 1H), 8.05-8.04 (m, 1H), 7.99 (d, J=8.8 Hz, 2H), 7.28 (d, J=3.4 Hz, 1H), 7.06 (d, J=8.9 Hz, 2H), 6.79 (dd, J=3.5, 1.8 Hz, 1H), 4.76 (hept, J=6.0 Hz, 1H), 1.30 (d, J=6.0 Hz, 6H). $^{13}$C NMR (200 MHz, DMSO-$d_6$) δ 164.2, 161.3, 157.5, 154.2, 146.7, 138.5, 130.5, 123.7, 115.1, 113.8, 112.5, 69.7, 21.7. ESI-MS: m/z 313.8 [M+H], HPLC retention time: 12.001 min. HPLC purity 97.3%.

4-methylthio-N-(5-(2,3-dihydrobenzo[b][1,4]dioxin-6-yl)-1,3,4-oxadiazol-2-yl)benzamide (23, AC10020)

Isolated as white solid (0.002 g, 0.005 mmol, 4%). $^1$H NMR (800 MHz, DMSO-$d_6$) δ 7.90 (t, J=1.8 Hz, 1H), 7.79 (d, J=7.3 Hz, 1H), 7.50-7.39 (m, 3H), 7.36 (d, J=2.0 Hz, 1H), 7.05 (d, J=8.4 Hz, 1H), 6.54 (s, 1H), 4.35-4.29 (m, 4H), 2.54 (s, 3H). $^{13}$C NMR (200 MHz, DMSO-$d_6$) δ 163.2, 146.0, 143.8, 138.4, 128.9, 128.8, 125.3, 124.9, 119.2, 118.1, 117.2, 114.3, 64.4, 64.1, 40.0, 14.64. ESI-MS: m/z 339.7 [M+H], HPLC retention time: 11.280 min. HPLC purity 97.9%.

N-(5-cyclohexyl-1,3,4-oxadiazol-2-yl)-3-(trifluoromethyl)benzamide (24, AC10021)

Isolated as white solid (0.035 g, 0.10 mmol, 43%). $^1$H NMR (500 MHz, DMSO-$d_6$): δ 12.52 (s, 1H), 8.36 (s, 1H), 8.31 (d, J=7.9 Hz, 1H), 8.01 (d, J=7.8 Hz, 1H), 7.79 (t, J=8.0 Hz, 1H), 2.94 (m, 1H), 2.01 (m, 2H), 1.75 (m, 2H), 1.69-1.62 (m, 1H), 1.53 (m, 2H), 1.43-1.36 (m, 2H), 1.32-1.23 (m, 1H). ESI-MS: 339.5 [M+]. HPLC retention time: 13.035 min. HPLC purity 95.6%.

N-(5-phenyl-1,3,4-oxadiazol-2-yl)-3-(trifluoromethyl)benzamide (25, AC10022)

Isolated as white solid (0.039 g, 0.119 mmol, 48%). $^1$H NMR (500 MHz, DMSO-$d_6$): δ 12.64 (s, 1H), 8.37 (s, 1H), 8.30 (d, J=7.7 Hz, 1H), 7.97-7.92 (m, 3H), 7.78-7.74 (m, 1H), 7.58 (bs, 3H). ESI-MS: 333.6 [M+]. HPLC retention time: 12.501 min. HPLC purity 99.3%.

N-(5-(2,3-dihydrobenzo[b][1,4]dioxin-6-yl)-1,3,4-oxadiazol-2-yl)-3-(trifluoromethyl)benzamide (26, AC10023)

Isolated as a white solid (0.013 g, 0.032 mmol, 18%). $^1$H NMR (500 MHz, DMSO-$d_6$): δ 12.59 (s, 1H), 8.40 (s, 1H), 8.33 (d, J=7.8 Hz, 1H), 8.03 (d, J=7.8 Hz, 1H), 7.81 (t, J=7.9 Hz, 1H), 7.45 (dd, J=8.5, 2.1 Hz, 1H), 7.40 (t, J=2.2 Hz, 1H), 7.09 (d, J=8.5 Hz, 1H), 4.34 (q, J=5.0 Hz, 4H). ESI-MS: 391.6 [M+]. HPLC retention time: 12.513 min. HPLC purity 99.1%.

N-(5-cyclohexyl-1,3,4-oxadiazol-2-yl)-3,4-dimethylbenzamide (27, AC10024)

Isolated as a white solid (0.018 g, 0.060 mmol, 25%). $^1$H NMR (500 MHz, Chloroform-d) δ 11.30 (s, 1H), 7.87 (s, 1H), 7.81 (d, J=8.0 Hz, 1H), 7.18 (d, J=7.2 Hz, 1H), 2.85 (broad s, 1H), 2.27 (s, 6H), 2.09-2.04 (m, 2H), 1.81-1.77 (m, 2H), 1.68-1.65 (m, 1H), 1.61-1.56 (m, 2H), 1.38-1.32 (m, 2H), 1.31-1.24 (m, 1H). ESI-MS: 299.6 [M+]. HPLC retention time: 13.038 min. HPLC purity 96%.

N-(5-cyclohexyl-1,3,4-oxadiazol-2-yl)-4-isopropoxybenzamide (28, AC10025)

Isolated as a white solid (0.018 g, 0.051 mmol, 18%). $^1$H NMR (800 MHz, DMSO-$d_6$) δ 11.63 (s, 1H), 7.96-7.93 (m, 2H), 7.03-7.00 (m, 2H), 4.73 (hept, J=6.0 Hz, 1H), 2.93-2.89 (m, 1H), 2.00-1.96 (m, 2H), 1.75-1.70 (m, 2H), 1.65-1.60 (m, 1H), 1.55-1.48 (m, 2H), 1.40-1.34 (m, 2H), 1.28 (d, J=5.9 Hz, 6H), 1.27-1.22 (m, 1H). $^{13}$C NMR (201 MHz, DMSO-d6) δ 166.97, 165.09 (d, J=43.9 Hz), 161.59, 158.34, 130.86, 124.59, 115.49, 70.08, 34.62, 29.89, 25.62, 25.07, 22.14. ESI-MS: 329.7 [M+]. HPLC retention time: 12.672 min. HPLC purity 95.1%.

N-(5-(5,6,7,8-tetrahydronaphthalen-2-yl)-1,3,4-oxadiazol-2-yl)-3-(trifluoromethyl)benzamide (29, AC10026)

Isolated as white solid (0.14 g, 0.035 mmol, 15%). $^1$H NMR (500 MHz, DMSO-$d_6$): δ 12.72 (s, 1H), 8.41 (s, 1H), 8.34 (d, J=7.9 Hz), 8.04 (d, J=7.9 Hz), 7.82 (t, J=7.8 Hz, 1H), 7.74-7.62 (m, 2H), 7.29 (d, J=7.9 Hz, 1H), 2.85-2.78 (m, 4H), 1.85-1.72 (m, 4H). ESI-MS: 387.9 [M+]. HPLC retention time: 13.823 min. HPLC purity 97.3%.

4-isopropoxy-N-(5-phenyl-1,3,4-oxadiazol-2-yl)benzamide (30, AC10027)

Isolated as white solid (0.010 g, 0.031 mmol, 12%). $^1$H NMR (500 MHz, DMSO-$d_6$): δ 12.01 (s, 1H), 8.02 (d, J=8.8 Hz, 2H), 7.98-7.96 (m, 2H), 7.62 (broad m, 3H), 7.06 (d, J=9.2 Hz, 2H), 4.79-4.74 (m, 1H), 1.31 (d, J=6.1 Hz, 6H). ESI-MS: 323.5 [M+]. HPLC retention time: 12.314 min. HPLC purity 99.1%.

N-(5-(4-fluorophenyl)-1,3,4-oxadiazol-2-yl)-3-(trifluoromethyl)benzamide (31, AC10028)

Isolated as white solid (0.022 g, 0.063 mmol, 28%). $^1$H NMR (500 MHz, DMSO-$d_6$): δ 12.72 (s, 1H), 8.40 (s, 1H), 8.34 (d, J=7.9 Hz, 1H), 8.06-8.00 (m, 3H), 7.80 (t, J=7.8 Hz, 1H), 7.47 (t, J=8.3 Hz, 2H). APCI-MS: 352.2 [M+H]. HPLC retention time: 12.643 min. HPLC purity 100%.

N-(5-(2,3-dihydrobenzo[b][1,4]dioxin-6-yl)-1,3,4-oxadiazol-2-yl)-4-methylbenzamide (32, AC10029)

Isolated as white solid (0.015 g, 0.044 mmol, 24%). $^1$H NMR (500 MHz, DMSO-$d_6$): δ 12.02 (s, 1H), 7.97-7.90 (m, 2H), 7.84-7.76 (m, 1H), 7.45 (t, J=8.3 Hz, 1H), 7.41-7.35

N-(5-(4-fluorophenyl)-1,3,4-oxadiazol-2-yl)-3,4-dimethylbenzamide (33, AC10030)

Isolated as white solid (0.015 g, 0.048 mmol, 25%). $^1$H NMR (500 MHz, DMSO-$d_6$): δ 11.99 (s, 1H), 8.00-7.96 (m, 2H), 7.80 (bs, 1H), 7.74 (d, J=7.8 Hz, 1H), 7.43 (t, J=8.9 Hz, 2H), 7.29 (d, J=7.9 Hz, 1H), 2.27 (s, 6H). ESI-MS: 311.5 [M+]. HPLC retention time: 12.304 min. HPLC purity 100%.

N-(5-(4-fluorophenyl)-1,3,4-oxadiazol-2-yl)-4-methylbenzamide (34, AC10031)

Isolated as white solid (0.016 g, 0.054 mmol, 42%). $^1$H NMR (500 MHz, DMSO-$d_6$) δ 12.10 (s, 1H), 8.05-8.02 (m, 2H), 7.96 (d, J=7.9 Hz, 2H), 7.49-7.45 (m, 2H), 7.38 (d, J=7.9 Hz, 2H), 2.41 (s, 3H). ESI-MS: 297.4 [M+]. HPLC retention time: 11.907 min. HPLC purity 99.2%.

N-(5-cyclohexyl-1,3,4-oxadiazol-2-yl)-4-methylbenzamide (35, AC10032)

Isolated as white solid (0.042 g, 0.15 mmol, 49%). $^1$H NMR (500 MHz, DMSO-$d_6$): δ 11.79 (s, 1H), 7.91 (broad d, J=8.4 Hz, 2H), 7.35 (broad d, J=7.9 Hz), 2.99-2.91 (m, 1H), 2.39 (s, 3H), 2.05-1.98 (m, 2H), 1.77-1.72 (m, 2H), 1.67-1.63 (m, 1H), 1.58-1.49 (m, 2H), 1.43-1.35 (m, 2H), 1.31-1.23 (m, 1H). ESI-MS: 285.6 [M+]. HPLC retention time: 12.163 min. HPLC purity 100%.

4-methyl-N-(5-(5,6,7,8-tetrahydronaphthalen-2-yl)-1,3,4-oxadiazol-2-yl)benzamide (36, AC10033)

Isolated as white solid (0.028 g, 0.084 mmol, 45%). $^1$H NMR (500 MHz, DMSO-$d_6$): δ 12.06 (s, 1H), 7.95 (d, J=7.9 Hz, 2H), 7.71-7.66 (m, 2H), 7.38 (d, J=8.0 Hz, 2H), 7.28 (d, J=8.0 Hz, 1H), 2.91-2.76 (broad m, 4H), 2.40 (s, 3H), 1.85-1.73 (broad m, 4H). ESI-MS: 333.5 [M+]. HPLC retention time: 13.244 min. HPLC purity 100%.

N-(5-(4-fluorophenyl)-1,3,4-oxadiazol-2-yl)-3-methoxybenzamide (37, AC10034)

Isolated as white solid (0.017 g, 0.054 mmol, 39%). $^1$H NMR (500 MHz, DMSO-$d_6$): δ 12.27 (s, 1H), 8.02 (m, 2H), 7.70-7.53 (m, 2H), 7.46 (m, 3H), 7.20 (m, 1H), 3.84 (s, 3H). ESI-MS: 313.8 [M+]. HPLC retention time: 11.669 min. HPLC purity 100%.

N-(5-(2,3-dihydrobenzo[b][1,4]dioxin-6-yl)-1,3,4-oxadiazol-2-yl)-3,4-dimethylbenzamide (38, AC10035)

Isolated as white solid (0.030 g, 0.085 mmol, 37%). $^1$H NMR (500 MHz, DMSO-$d_6$): δ 11.93 (s, 1H), 7.80 (s, 1H), 7.73 (d, J=8.0 Hz, 1H), 7.40 (dd, J=8.4, 2.1 Hz, 1H), 7.35 (bs, 1H), 7.27 (d, J=7.9 Hz, 1H), 7.04 (d, J=8.5 Hz), 4.30 (m, 4H), 2.27 (s, 3H), 2.05 (s, 3H). ESI-MS: 351.8 [M+] HPLC retention time: 12.094 min. HPLC purity 100%.

N-(5-(4-fluorophenyl)-1,3,4-oxadiazol-2-yl)-4-(piperidin-1-ylsulfonyl)benzamide (39, AC10036)

Isolated as white solid (0.006 g, 0.014 mmol, 5%). $^1$H NMR (500 MHz, DMSO-$d_6$) δ 8.35 (d, J=2.0 Hz, 1H), 8.31 (d, J=7.8 Hz, 1H), 8.01-7.88 (m, 4H), 7.76 (t, J=7.8 Hz, 1H), 7.48-7.37 (m, 2H), 3.02-2.82 (m, 4H), 1.52 (m, J=5.8 Hz, 4H), 1.33 (m, J=8.1 Hz, 2H). ESI-MS: 331.2 [M+] HPLC retention time: 12.527 min. HPLC purity 96.1%.

N-(5-(2,3-dihydrobenzo[b][1,4]dioxin-6-yl)-1,3,4-oxadiazol-2-yl)-4-isopropoxybenzamide (40, AC10037)

Isolated as white solid (0.020 g, 0.052 mmol, 23%). $^1$H NMR (500 MHz, DMSO-$d_6$): δ 12.00 (s, 1H), 8.01-7.99 (m, 2H), 7.44-7.35 (m, 2H), 7.08-7.01 (m, 3H), 4.77-4.72 (broad m, 1H), 4.36-4.32 (broad m, 4H), 1.30 (d, J=6.0 Hz, 6H). ESI-MS: 382.1 [M+H]$^+$ HPLC retention time: 12.247 min. HPLC purity 100%.

N-(5-(2,3-dihydrobenzo[b][1,4]dioxin-6-yl)-1,3,4-oxadiazol-2-yl)-3-methoxybenzamide (41, AC10038)

Isolated as white solid (0.025 g, 0.071 mmol, 35%). $^1$H NMR (500 MHz, DMSO-$d_6$): δ 12.36 (s, 1H), 7.69-7.64 (m, 2H), 7.46-7.38 (m, 2H), 7.18-7.09 (m, 2H), 6.62 (s, 1H), 4.41-4.34 (m, 4H), 3.86 (s, 3H). ESI-MS: 354.1 [M+H]$^+$ HPLC retention time: 11.457 min. HPLC purity 95.6%.

N-(5-(4-fluorophenyl)-1,3,4-oxadiazol-2-yl)-4-methoxybenzamide (42, AC10039)

Isolated as white solid (0.032 g, 0.10 mmol, 52%). $^1$H NMR (500 MHz, DMSO-$d_6$): δ 12.01 (s, 1H), 8.04 (broad m, 4H), 7.47 (t, J=8.7 Hz, 2H), 7.11 (broad m, 2H), 3.86 (s, 3H). ESI-MS: 355.2 [M+CH$_3$CN+H]$^+$. HPLC retention time: 11.533 min. HPLC purity 98.4%.

N-(5-cyclohexyl-1,3,4-oxadiazol-2-yl)-4-methoxybenzamide (43, AC10040)

Isolated as white solid (0.022 g, 0.073 mmol, 38%). $^1$H NMR (500 MHz, DMSO-$d_6$) δ 11.73 (s, 1H), 8.02 (d, J=8.5 Hz, 2H), 7.10 (d, J=8.6 Hz, 2H), 3.87 (s, 3H), 2.96 (broad m, 1H), 2.04-1.99 (broad m, 1H), 1.78-1.76 (broad m, 2H), 1.69-1.66 (broad m, 1H), 1.59-1.50 (m, 2H), 1.45-1.38 (m, 2H), 1.33-1.16 (m, 2H). ESI-MS: 300.0 [M−H]$^−$. HPLC retention time: 11.795 min. HPLC purity 95.2%.

4-methoxy-N-(5-(5,6,7,8-tetrahydronaphthalen-2-yl)-1,3,4-oxadiazol-2-yl)benzamide (44, AC10041)

Isolated as white solid (0.047 g, 0.13 mmol, 58%). $^1$H NMR (500 MHz, DMSO-$d_6$) δ 8.04 (d, J=8.3 Hz, 1H), 7.91 (d, J=8.4 Hz, 1H), 7.69-7.59 (m, 2H), 7.23 (dd, J=52.5, 7.9 Hz, 1H), 7.08 (dd, J=23.4, 8.4 Hz, 2H), 3.83 (s, 3H), 2.78 (s, 4H), 1.77 (d, J=4.4 Hz, 4H). APCI-MS=350.3 [M+H]$^+$. HPLC retention time: 12.242 min. HPLC purity 100%.

4-ethyl-N-(5-(4-fluorophenyl)-1,3,4-oxadiazol-2-yl)benzamide (45, AC10044)

Isolated as white solid (0.048 g, 0.15 mmol, 55%). 1H NMR (800 MHz, DMSO-$d_6$) δ 12.06 (s, 1H), 8.04-8.02 (m, 2H), 7.97 (d, J=7.8 Hz, 2H), 7.48-7.45 (m, 2H), 7.41 (d, J=7.8 Hz, 2H), 2.71 (q, J=7.6 Hz, 2H), 1.22 (t, J=7.6 Hz, 3H). APCI-MS=312.2 [M+H]$^+$. HPLC retention time: 12.433 min. HPLC purity 100%.

N-(5-cyclohexyl-1,3,4-oxadiazol-2-yl)-4-ethylbenzamide (46, AC10045)

Isolated as white solid (0.020 g, 0.066 mmol, 29%). $^1$H NMR (500 MHz, DMSO-$d_6$): δ 11.89 (s, 1H), 7.93 (d, J=8.0 Hz, 2H), 7.38 (d, J=8.0 Hz, 2H), 2.96-2.90 (broad m, 1H), 2.69 (q, J=7.7 Hz, 2H), 2.02-1.98 (broad m, 2H), 1.77-1.73 (broad m, 2H), 1.67-1.63 (broad m, 1H), 1.57-1.49 (m, 2H), 1.43-1.35 (m, 2H), 1.31-1.26 (broad m, 1H), 1.21 (t, J=7.6 Hz, 3H). ESI-MS=300.2 [M+H]$^+$ HPLC retention time: 12.732 min. HPLC purity 95.5%.

3-fluoro-N-(5-(4-fluorophenyl)-1,3,4-oxadiazol-2-yl)benzamide (47, AC10046)

Isolated as white solid (0.033 g, 0.11 mmol, 62%). $^1$H NMR (500 MHz, DMSO-$d_6$) δ 8.05-8.02 (broad m, 2H), 7.90 (d, J=7.6 Hz, 1H), 7.85 (d, J=9.8 Hz, 1H), 7.66-7.62 (broad m, 1H), 7.56-7.52 (broad m, 1H), 7.51-7.45 (broad m, 2H). ESI-MS: 365.1 [M+CH$_3$CN+H]$^+$. HPLC retention time: 11.823 min. HPLC purity 96.7%.

N-(5-cyclohexyl-1,3,4-oxadiazol-2-yl)-3-fluorobenzamide (48, AC10047)

Isolated as white solid (0.034 g, 0.12 mmol, 49%). $^1$H NMR (500 MHz, DMSO-$d_6$): δ 12.04 (s, 1H), 7.86 (d, J=7.8 Hz, 1H), 7.81-7.79 (m, 1H), 7.65-7.57 (m, 1H), 7.51 (t, J=8.6 Hz, 1H), 2.96-2.92 (broad m, 1H), 2.02-1.99 (broad m, 2H), 1.77-1.72 (broad m, 2H), 1.67-1.63 (broad m, 1H), 1.57-1.49 (m, 2H), 1.43-1.35 (m, 2H), 1.31-1.23 (m, 1H). APCI-MS=290.2 [M+H]$^+$. HPLC retention time: 12.425 min. HPLC purity 98.2%.

4-fluoro-N-(5-(4-fluorophenyl)-1,3,4-oxadiazol-2-yl)benzamide (49, AC10052)

Isolated as white solid (0.052 g, 0.17 mmol, 62%). $^1$H NMR (500 MHz, DMSO-$d_6$): δ 12.25 (s, 1H), 8.13 (broad m, 2H), 8.03 (broad m, 2H), 7.48 (t, J=8.6 Hz, 2H), 7.42 (t, J=8.7 Hz, 2H). APCI-MS=302.2 [M+H]$^+$. HPLC retention time: 11.695 min. HPLC purity 100%.

N-(5-cyclohexyl-1,3,4-oxadiazol-2-yl)-4-fluorobenzamide (50, AC10053) Isolated as white solid (0.026 g, 0.090 mmol, 43%). $^1$H NMR (500 MHz, DMSO-$d_6$): δ 12.13 (s, 1H), 8.15-8.04 (m, 2H), 7.42-7.34 (m, 2H), 2.98-2.93 (broad m, 1H), 2.04-1.99 (broad m, 2H), 1.78-1.73 (broad m, 2H), 1.67-1.64 (broad m, 1H), 1.561-1.51 (m, 2H), 1.44-136 (m, 2H), 1.31-1.24 (m, 1H). ESI-MS: 290.1 [M+H]$^+$. HPLC retention time: 12.251 min. HPLC purity 98.9%.

4-chloro-N-(5-(4-fluorophenyl)-1,3,4-oxadiazol-2-yl)benzamide (51, AC10054)

Isolated as white solid (0.043 g, 0.14 mmol, 48%). $^1$H NMR (500 MHz, DMSO-$d_6$): δ 12.31 (s, 1H), 8.07-8.02 (m, 4H), 7.73-7.62 (m, 2H), 7.47 (t, J=8.7 Hz, 2H). APCI-MS=318.1 [M+H]$^+$. HPLC retention time: 12.269 min. HPLC purity 99.1%.

4-chloro-N-(5-cyclohexyl-1,3,4-oxadiazol-2-yl)benzamide (52, AC10055)

Isolated as white solid (0.030 g, 0.098 mmol, 41%). $^1$H NMR (800 MHz, DMSO-$d_6$) δ 11.98 (m, 1H), 8.02 (d, J=8.2 Hz, 2H), 7.62 (d, J=8.2 Hz, 2H), 2.94-2.92 (broad m, 1H), 2.01-2.00 (broad m, 2H), 1.76-1.73 (broad m, 2H), 1.65-1.64 (m, 1H), 1.56-1.51 (m, 2H), 1.41-1.37 (m, 2H), 1.29-1.25 (m, 1H). ESI-MS: 370.2 [M+CH$_3$CN+Na]$^+$. HPLC retention time: 12.639 min. HPLC purity 98%.

4-fluoro-N-(5-(5,6,7,8-tetrahydronaphthalen-2-yl)-1,3,4-oxadiazol-2-yl)benzamide (53, AC10056)

Isolated as white solid (0.020 g, 0.059 mmol, 28%). $^1$H NMR (500 MHz, DMSO-$d_6$): δ 8.13-8.09 (broad m, 2H), 7.70-7.64 (broad m, 2H), 7.46-7.35 (broad m, 2H), 7.30-7.26 (broad m, 1H), 2.83-2.78 (broad m, 4H), 1.81-1.74 (broad m, 4H). ESI-MS: 338.2 [M+H]$^+$. HPLC retention time: 12.785 min. HPLC purity 97.9%.

3-fluoro-N-(5-(5,6,7,8-tetrahydronaphthalen-2-yl)-1,3,4-oxadiazol-2-yl)benzamide (54, AC10059)

Isolated as white solid (0.024 g, 0.071 mmol, 36%). $^1$H NMR (800 MHz, DMSO-$d_6$) δ 7.90 (d, J=7.7 Hz, 1H), 7.83 (d, J=9.8 Hz, 1H), 7.66 (d, J=7.8 Hz, 1H), 7.65 (s, 1H), 7.62-7.59 (m, 1H), 7.52-7.48 (m, 1H), 7.28 (d, J=7.9 Hz, 1H), 2.82-2.79 (broad m, 4H), 1.78-1.76 (m, 4H). ESI-MS: 338.2 [M+H]$^+$. HPLC retention time: 13.239 min. HPLC purity 97.7%.

2-fluoro-N-(5-(4-fluorophenyl)-1,3,4-oxadiazol-2-yl)benzamide (55, AC10060)

Isolated as white solid (0.009 g, 0.031 mmol, 14%). $^1$H NMR (500 MHz, DMSO-$d_6$): δ 12.33 (s, 1H), 8.00-7.95 (m, 2H), 7.81-7.70 (m, 1H), 7.67-7.60 (m, 1H), 7.46-7.41 (m, 2H), 7.37-7.31 (m, 2H). ESI-MS: 302.2 [M+H]$^+$. HPLC retention time: 11.474 min. HPLC purity 99.5%.

4-chloro-N-(5-(5,6,7,8-tetrahydronaphthalen-2-yl)-1,3,4-oxadiazol-2-yl)benzamide (56, AC10061)

Isolated as white solid (0.047 g, 0.13 mmol, 57%). $^1$H NMR (500 MHz, DMSO-$d_6$): δ 8.07 (d, J=8.1 Hz, 2H), 7.69-7.62 (m, 4H), 7.29 (d, J=7.9 Hz, 1H), 2.81 (broad m, 4H), 1.77 (m, 4H). ESI-MS: 355.3 [M+H]$^+$. HPLC retention time: 13.573 min. HPLC purity 99%.

4-ethyl-N-(5-(5,6,7,8-tetrahydronaphthalen-2-yl)-1,3,4-oxadiazol-2-yl)benzamide (57, AC10062)

Isolated as white solid (0.032 g, 0.093 mmol, 40%). $^1$H NMR (500 MHz, DMSO-$d_6$): δ 7.93 (m, 2H), 7.62 (m, 2H), 7.35 (d, J=7.9 Hz, 2H), 7.24 (d, J=8.0 Hz, 1H), 2.82-2.74 (m, 4H), 2.66 (q, J=7.6 Hz, 2H), 1.74-1.71 (broad m, 4H), 1.18 (t, J=7.5 Hz, 3H). APCI-MS: 348.3 [M+H]$^+$. HPLC retention time: 13.239 min. HPLC purity 97.7%.

N-(5-cyclohexyl-1,3,4-oxadiazol-2-yl)-[1,1'-biphenyl]-3-carboxamide (58, AC10063)

Isolated as white solid (0.032 g, 0.092 mmol, 31%). $^1$H NMR (500 MHz, DMSO-$d_6$): δ 12.06 (s, 1H), 8.33 (m, 1H), 7.99 (m, 2H), 7.80 (m, 2H), 7.66 (m, 1H), 7.54 (m, 2H), 7.44 (q, J=6.8 Hz, 1H), 2.99-2.94 (m, 1H), 2.04-2.02 (broad m, 2H), 1.78-1.77 (broad m, 2H), 1.68-165 (m, 1H), 1.60-1.52 (m, 2H), 1.45-1.37 (m, 2H), 1.32-1.25 (m, 1H). APCI-MS: 348.3 [M+H]$^+$. HPLC retention time: 13.318 min. HPLC purity 99.2%.

N-(5-(4-fluorophenyl)-1,3,4-oxadiazol-2-yl)-[1,1'-biphenyl]-3-carboxamide (59, AC10064)

Isolated as white solid (0.043 g, 0.120 mmol, 43%). $^1$H NMR (500 MHz, DMSO-$d_6$): δ 12.36 (s, 1H), 8.38 (s, 1H), 8.08-7.99 (m, 4H), 7.83 (d, J=7.7 Hz, 2H), 7.69 (t, J=7.8 Hz, 1H), 7.51-7.44 (t, J=7.6 Hz, 2H), 7.47 (m, 3H). APCI-MS: 360.2 [M+H]$^+$. HPLC retention time: 13.009 min. HPLC purity 100%.

N-(5-(4-fluorophenyl)-1,3,4-oxadiazol-2-yl)-3-methyl-5-(trifluoromethyl)benzamide (60, AC10065)

Isolated as white solid (0.026 g, 0.071 mmol, 40%). $^1$H NMR (500 MHz, DMSO-d$_6$): δ 12.46 (s, 1H), 8.24-8.16 (broad m, 2H), 8.06-8.02 (broad m, 2H), 7.88 (s, 1H), 7.56-7.44 (broad m, 2H), 2.50 (s, 3H). ESI-MS: 366.1 [M+H]$^+$. HPLC retention time: 13.050 min. HPLC purity 100%.

N-(5-(4-fluorophenyl)-1,3,4-oxadiazol-2-yl)-[1,1'-biphenyl]-4-carboxamide (61, AC10066)

Isolated as white solid (0.045 g, 0.13 mmol, 45%). 1H NMR (500 MHz, DMSO-d$_6$): δ 12.31 (s, 1H), 8.13 (d, J=8.1 Hz, 2H), 8.03-7.99 (m, 2H), 7.85 (d, J=8.1 Hz, 2H), 7.76 (d, J=7.8 Hz, 2H), 7.51-7.40 (m, 5H). APCI-MS: 360.2 [M+H]$^+$. HPLC retention time: 12.916 min. HPLC purity 96.1%.

N-(5-(4-fluorophenyl)-1,3,4-oxadiazol-2-yl)-4-methyl-3-(trifluoromethyl)benzamide (62, AC10067)

Isolated as white solid (0.039 g, 0.11 mmol, 38%). $^1$H NMR (500 MHz, DMSO-d$_6$): δ 12.48 (s, 1H), 8.35 (s, 1H), 8.22 (d, J=8.0 Hz, 1H), 8.04-8.02 (m, 2H), 7.66 (d, J=8.0 Hz, 1H), 7.47 (t, J=8.5 Hz, 2H), 2.51 (s, 3H). APCI-MS: 366.2 [M+H]$^+$. HPLC retention time: 12.974 min. HPLC purity 96.4%.

N-(5-(4-fluorophenyl)-1,3,4-oxadiazol-2-yl)-3-methoxy-5-(trifluoromethyl)benzamide (63, AC10068)

Isolated as white solid (0.032 g, 0.084 mmol, 30%). $^1$H NMR (500 MHz, DMSO-d$_6$): δ 12.50 (s, 1H), 8.04-8.02 (m, 2H), 7.96 (s, 1H), 7.87 (s, 1H), 7.55 (s, 1H), 7.48 (t, J=8.7 Hz, 2H), 3.94 (s, 3H). APCI-MS: 382.2 [M+H]$^+$. HPLC retention time: 12.981 min. HPLC purity 100%.

N-(5-cyclohexyl-1,3,4-oxadiazol-2-yl)-3-methyl-5-(trifluoromethyl)benzamide (64, AC10069)

Isolated as white solid (0.022 g, 0.062 mmol, 29%). $^1$H NMR (500 MHz, DMSO-d$_6$): δ 10.52 (s, 1H), 8.00 (broad s, 2H), 7.79 (s, 1H), 2.46 (s, 3H), 2.30-2.24 (m, 1H), 1.77-1.72 (broad m, 4H), 1.65-1.63 (broad m, 1H), 1.43-1.36 (m, 2H), 1.27-1.17 (m, 4H). APCI-MS: 354.2 [M+H]$^+$. HPLC retention time: 12.195 min. HPLC purity 98.5%.

N-(5-cyclohexyl-1,3,4-oxadiazol-2-yl)-3-methoxy-5-(trifluoromethyl)benzamide (65, AC10070)

Isolated as white solid (0.024 g, 0.065 mmol, 22%). $^1$H NMR (500 MHz, DMSO-d$_6$): δ 12.52 (s, 1H), 7.92 (s, 1H), 7.84 (s, 1H), 7.50 (s, 1H), 3.35 (s, 3H), 2.94-2.90 (m, 1H), 2.04-1.98 (m, 2H), 1.77-1.73 (m, 2H), 1.66-1.62 (m, 1H), 1.57-1.49 (m, 2H), 1.43-1.35 (m, 2H), 1.31-1.23 (m, 1H). APCI-MS: 370.3 [M+H]$^+$. HPLC retention time: 13.338 min. HPLC purity 98.6%.

N-(5-cyclohexyl-1,3,4-oxadiazol-2-yl)-4-methyl-3-(trifluoromethyl)benzamide (66, AC10071)

Isolated as white solid (0.016 g, 0.045 mmol, 25%). $^1$H NMR (500 MHz, DMSO-d$_6$) δ 12.37 (s, 1H), 8.31 (s, 1H), 8.18 (d, J=8.1 Hz, 1H), 7.60 (d, J=8.1 Hz, 1H), 2.94-2.88 (m, 1H), 2.52 (s, 3H), 2.01-1.98 (m, 2H), 1.76-1.73 (m, 2H), 1.66-1.62 (m, 1H), 1.57-1.49 (m, 2H), 1.43-1.35 (m, 2H), 1.31-1.23 (m, 1H). APCI-MS: 354.2 [M+H]$^+$. HPLC retention time: 13.367 min. HPLC purity 95.8%.

3-methyl-N-(5-(5,6,7,8-tetrahydronaphthalen-2-yl)-1,3,4-oxadiazol-2-yl)-5-(trifluoromethyl)benzamide (67, AC10072)

Isolated as white solid (0.018 g, 0.045 mmol, 32%). $^1$H NMR (500 MHz, DMSO-d$_6$): δ 12.44 (s, 1H), 8.19-8.16 (broad m, 2H), 7.87 (s, 1H), 7.68-7.66 (m, 2H), 7.29 (d, J=7.9 Hz, 1H), 2.85-2.80 (broad m, 4H), 2.50 (s, 3H), 1.79-1.76 (m, 4H). APCI-MS: 402.2 [M+H]$^+$. HPLC retention time: 12.963 min. HPLC purity 100%.

4-methyl-N-(5-(5,6,7,8-tetrahydronaphthalen-2-yl)-1,3,4-oxadiazol-2-yl)-3-(trifluoromethyl)benzamide (68, AC10073)

Isolated as white solid (0.056 g, 0.14 mmol, 60%). $^1$H NMR (500 MHz, DMSO-d$_6$): δ 12.55 (s, 1H), 8.35 (s, 1H), 8.22 (d, J=8.1 Hz, 1H), 7.68-7.65 (m, 3H), 7.28 (d, J=7.9 Hz, 1H), 2.83-2.75 (broad m, 4H), 2.51 (s, 3H), 1.78-1.76 (m, 4H). APCI-MS: 402.2 [M+H]$^+$. HPLC retention time: 14.099 min. HPLC purity 97.1%.

3-methoxy-N-(5-(5,6,7,8-tetrahydronaphthalen-2-yl)-1,3,4-oxadiazol-2-yl)-5-(trifluoromethyl)benzamide (69, AC10074)

Isolated as white solid (0.041 g, 0.098 mmol, 42%). $^1$H NMR (500 MHz, DMSO-d$_6$): δ 12.53 (s, 1H), 7.96 (s, 1H), 7.87 (s, 1H), 7.68-7.65 (m, 2H), 7.54 (s, 1H), 7.28 (d, J=8.0 Hz, 1H), 3.94 (s, 3H), 2.84-2.80 (broad m, 4H), 1.78-1.76 (m, 4H). APCI-MS: 418.2 [M+H]+. HPLC retention time: 14.048 min. HPLC purity 100%.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A compound having a formula

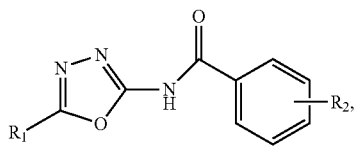
(I)

or a pharmaceutically acceptable salt thereof, wherein $R_1$ is an alkyl, alkenyl, alkynyl, heteroalkyl, heteroalkenyl, heteroalkynyl, cycloalkyl, heterocyclyl, or an optionally substituted aryl, arylalkyl, or arylalkenyl;

$R_2$ represents five substituents independently selected from the group consisting of hydrogen, halo, hydroxy, amino, nitro, cyano, thio, alkyl, alkenyl, alkynyl, heteroalkyl, heteroalkenyl, heteroalkynyl, cycloalkyl, heterocyclyl, alkoxyl, alkylamino, alkylthio, haloalkyl, alkylsulfide, sulphonyl, sulfonamide, alkylsulfonamide, or an optionally substituted aryl, arylalkyl, or arylalkenyl; or any two adjacent substituents that are taken together with the attached carbons to form an optionally substituted cycle or heterocycle and each of other substituents is defined as above; and wherein said compound is selected from the group consisting of

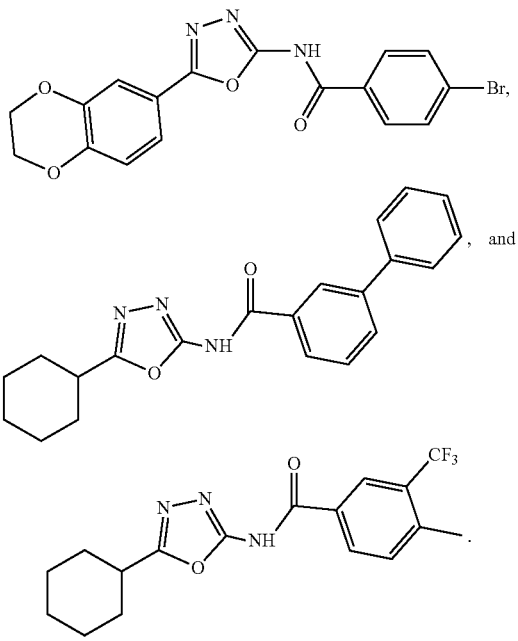

2. A pharmaceutical composition comprising one or more compounds of claim 1, or a pharmaceutically acceptable salt thereof, together with one or more diluents, excipients or carriers.

* * * * *